(12) United States Patent
Pillay et al.

(10) Patent No.: US 9,808,418 B2
(45) Date of Patent: Nov. 7, 2017

(54) PHARMACEUTICAL DOSAGE FORM

(75) Inventors: Viness Pillay, Gauteng (ZA); Rubina Perveen Shaikh, Gauteng (ZA); Yahya Essop Choonara, Gauteng (ZA); Lisa Claire Du Toit, Gauteng (ZA)

(73) Assignee: UNIVERSITY OF THE WITWATERSRAND, JOHANNESBURG, Johannesburg Gauteng (ZA)

( * ) Notice: Subject to any disclaimer, the term of this patent is extended or adjusted under 35 U.S.C. 154(b) by 671 days.

(21) Appl. No.: 13/988,959

(22) PCT Filed: Nov. 28, 2011

(86) PCT No.: PCT/IB2011/055331
§ 371 (c)(1),
(2), (4) Date: Sep. 3, 2013

(87) PCT Pub. No.: WO2012/070028
PCT Pub. Date: May 31, 2012

(65) Prior Publication Data
US 2013/0337022 A1 Dec. 19, 2013

(30) Foreign Application Priority Data
Nov. 26, 2010 (ZA) ................................ 2010/03740

(51) Int. Cl.
A61K 9/00 (2006.01)
A61K 9/52 (2006.01)

(52) U.S. Cl.
CPC ................ *A61K 9/00* (2013.01); *A61K 9/006* (2013.01); *A61K 9/0065* (2013.01)

(58) Field of Classification Search
CPC ......... A61K 9/006; A61K 9/00; A61K 9/0065
See application file for complete search history.

(56) References Cited

U.S. PATENT DOCUMENTS 7,097,851 B1 8/2006 Takada
2010/0254961 A1 10/2010 Nishio et al.

FOREIGN PATENT DOCUMENTS

| JP | 2002-531394 A | 8/2001 | | |
|---|---|---|---|---|
| JP | 2003-521493 A | 7/2003 | | |
| WO | WO 00/32172 A1 | 6/2000 | | |
| WO | WO 01/54667 A1 | 8/2001 | | |
| WO | WO2004028508 | * | 4/2004 | ............... A61K 9/20 |
| WO | WO 2004/041118 A2 | 5/2004 | | |
| WO | WO 2009/153633 A1 | 12/2009 | | |
| WO | WO 2010/002418 A2 | 1/2010 | | |

OTHER PUBLICATIONS

Ding, Nanosc. PVA Fiber Electrosp. Method, J of Polym. Sci. p. 1261,2002.*
Davis, "Formulation strategies for absorption windows", DDT, vol. 10, No. 4, Feb. 2005, pp. 249-257.
Frenot et al., "Polymer nanofibers assembled by electrospinning", Current Opinion in Colloid and Interface Science, vol. 8, 2003, pp. 64-75.
Guggi et al., "Systemic peptide delivery via the stomach: in vivo evaluation of an oral dosage form for salmon calcitonin", Journal of Controlled Release, vol. 92, 2003, pp. 125-135.
Patel et al., "Stomach Specific Anti-Helicobacter Pylori Therapy: Preparation and Evaluation of Amoxicillin-Loaded Chitosan Mucoadhesive Microspheres", Current Drug Delivery, vol. 4, No. 1, 2007, pp. 41-50.
Schmaljohann, "Thermo- and pH-responsive polymers in drug delivery", Advanced Drug Delivery Reviews, vol. 58, 2006, (Available online Oct. 18, 2006), pp. 1655-1670.
Shen et al., "Intestinal Patches for Oral Drug Delivery", Pharmaceutical Research, vol. 19, No. 4, Apr. 2002, pp. 391-395 (Abstract and pp. 391 and 392 only provided).
Ignatious et al., "Electrospun Nanofibers in Oral Drug Delivery," Pharmaceutical Research, vol. 27, No. 4, Apr. 2010, pp. 576-588.
Japanese Office Action, dated Sep. 24, 2014, for Japanese Application No. 2013-540480.
Yu et al., "Electrospun nanofiber-based drug delivery systems," Health, vol. 1, No. 2, 2009, pp. 67-75.
Nagy et al., "Electrospun water soluble polymer mat for ultrafast release of Donepezil HCl", eXPRESS Polymer Letters, vol. 4, No. 12 (2010) pp. 763-772.
Supplemental European Search Report issued in European Patent Application No. 11 84 2556 dated May 12, 2014.
Diaz De Leon et al., "Electrospinning Nanofibers of Polyaniline and Polyaniline/(Polystyrene and Polyethylene Oxide) Blends," Proceeding of the National Conference on Undergraduate Research (NCUR) 2001, Mar. 15-17, 2001, Lexington, Kentucky, (5 pages).
Eiamtrakarn et al., "Gastrointestinal mucoadhesive patch system (GI-MAPS) for oral administration of G-CSF, a model protein," Biomaterials, vol. 23, No. 1, Jan. 2002, pp. 145-152.

(Continued)

*Primary Examiner* — David J Blanchard
*Assistant Examiner* — Thurman Wheeler
(74) *Attorney, Agent, or Firm* — Birch, Stewart, Kolasch & Birch, LLP

(57) ABSTRACT

A pH responsive and mucoadhesive pharmaceutical dosage form for the release of a pharmaceutically active agent is described. The dosage form includes a mucoadhesive layer for site-specific mucoadhesion, a water-insoluble outer layer, and an intermediate layer including one or more pharmaceutically active agents for site-specific delivery. The different membranous layers perform different functions in order to create a drug delivery system which is able to deliver a drug to a specific site, for a particular period of time and with a specific drug release pattern. The dosage form can have two or more intermediate layers, each layer comprising an active agent. The mucoadhesive layer can also include an active agents. The dosage form is preferably an oral or buccal delivery form for release of the active agent into the gastro intestinal tract. The intermediate layer can be an electrospun fibrous membrane layer containing the active agent.

25 Claims, 14 Drawing Sheets

(56) References Cited

OTHER PUBLICATIONS

Grabovac et al., "Design and in vivo evaluation of a patch delivery system for insulin based on thiolated polymers," International Journal of Pharmaceutics, vol. 348, 2008, pp. 169-174.

International Search Report for International Application No. PCT/IB2011/055331, dated Apr. 16, 2012.

Shaikh et al., "A pH-responsive Mucoadhesive Membrane for Prolonged Oral Drug Delivery," Oct. 26, 2010, (1 page).

Shaikh et al., Conference Abstract, A pH-responsive Mucoadhesive Membrane for Prolonged Oral Drug Delivery, Abstract 123, Oct. 26, 2010, pp. 22.

Sun et al., "Electrospun Nanofibers Bundles," Proceedings of the 1st IEEE International Conference on Nano/Micro Engineered and Molecular Systems, Jan. 18-21, 2006, Zhuhai, China, pp. 1322-1326.

Helliwell, "The use of bioadhesives in targeted delivery within the gastrointestinal tract," Advanced Drug Delivery Reviews, vol. 11, 1993, pp. 221-251.

Hennink et al., "Novel crosslinking methods to design hydrogels," Advanced Drug Delivery Reviews, vol. 64, 2012 (Available online Sep. 13, 2012), pp. 223-236.

Kim et al., "Controlled protein release from electrospun biodegradable fiber mesh composed of poly(ϵ-caprolactone) and poly(ethylene oxide)," International Journal of Pharmaceutics, vol. 338, 2007 (Available online Feb. 2, 2007), pp. 276-283.

Nakamura et al., "Development of an oral sustained release drug delivery system utilizing pH-dependent swelling of carboxyvinyl polymer," Journal of Controlled Release, vol. 111, 2006 (Available online Feb. 13, 2006), pp. 309-315.

Rastogi et al., "Alginate microspheres of isoniazid for oral sustained drug delivery," International Journal of Pharmaceutics, vol. 334, 2007 (Available online Oct. 21, 2006), pp. 71-77.

Schmitz et al., "Oral Heparin Delivery: Design and In Vivo Evaluation of a Stomach-Targeted Mucoadhesive Delivery System," Journal of Pharmaceutical Sciences, vol. 94, No. 5, May 2005, pp. 966-973.

Sill et al., "Electrospinning: Applications in drug delivery and tissue engineering," Review, Biomaterials, vol. 29, 2008 (Available online Feb. 20, 2008), pp. 1989-2006.

Stamatialis et al., "Medical applications of membranes: Drug delivery, artificial organs and tissue engineering," Journal of Membrane Science, vol. 308, 2008 (Available online Oct. 3, 2007), pp. 1-34.

* cited by examiner

PHARMACEUTICAL DOSAGE FORM

FIELD OF THE INVENTION

The present invention relates to the application of a mucoadhesive membrane incorporating drug loaded electrospun fibres in developing an oral or buccal drug delivery system for improving the oral or buccal bioavailability of drugs and pharmaceutically active agents.

BACKGROUND TO THE INVENTION

Oral or buccal drug delivery is a highly favoured route of drug administration in the pharmaceutical industry due to factors such as patient preference for the oral route over other routes of drug administration. Patient compliance with oral drug delivery is a result of low cost, the ease and avoidance of pain upon administration, as well as a decrease in the risk of infections that are associated with parenteral dosage forms. Furthermore, the relatively large fluid volume available, the increased mucosal area available for absorption and the profuse blood supply to the gastric mucosa aids the absorption of many drugs. The success of orally delivered drugs is principally dependant on the transit of the drug delivery system (DDS) through the GIT. In addition to this, many drugs are absorbed at specific sites within the gastro intestinal tract (GIT) i.e. narrow absorption window (NAW) drugs. As conventional tablets and capsules are transported through the GIT, they release the drug into non-specific regions within the GIT. If the drug is not released in sufficient quantities at the site of absorption, the drug will not reach effective plasma drug concentrations to achieve the desired therapeutic effect. Thus many drugs are poorly absorbed, such as NAW drugs or drugs which are sensitive to gastric juices and enzymes, i.e. proteins and peptides. In many instances, oral prolonged release formulations provide lower bioavailability as compared to immediate release formulations, as release from the prolonged release formulations is not completed during transit of the delivery system through the GIT [5]. In addition, conventional drug delivery systems deliver drug in a peak-to-trough pattern, with the peaks usually being above the required dose, and therefore prolonged release systems would be preferred to relatively fast release systems [6].

SUMMARY OF THE INVENTION

According to a first embodiment of the invention, there is provided a pharmaceutical dosage form for the release of a pharmaceutically active agent comprising:
- a mucoadhesive layer which is capable of adhering to the gastro intestinal tract or buccal mucosa of the human or animal body;
- a water-insoluble outer layer; and
- an intermediate layer comprising a pharmaceutically active agent, wherein the intermediate layer is positioned between the mucoadhesive and water-insoluble outer layers.

The dosage form may comprise more than one active agent.

The dosage form may comprise two or more intermediate layers, each intermediate layer comprising an active agent.

One or more of the mucoadhesive layer, intermediate layer and water-insoluble outer layer may be in the form of a polymeric membrane.

One or more of the mucoadhesive layer, intermediate layer and water-insoluble outer layer may be formed from a stimulus-responsive polymer which targets the pharmaceutical dosage form to a specific region of the gastro intestinal tract, such as the gastric region or the intestinal region.

Each layer may be independently formed from one or more of the polymers selected from polyethylene oxide (PEO), polyvinyl alcohol (PVA), ethylcellulose (EC), poly (lactic) co-glycolic acids (PLGA), polylactic acids (PLA), polymethacrylates, polycaprolactones, polyesters and polyamides. The polymers may be crosslinked so as to retard the release of the active agent from the dosage form.

The polymers forming at least one of the polymeric membranes may be selected so as to render the pharmaceutical dosage form pH responsive and to thus facilitate delivery of the active agent to a specific region.

The mucoadhesive layer may comprise a polymeric membrane selected from polyacrylic acid, chitosan, pectin, hydroxypropylcellulose (HPC), hydroxypropylmethylcellulose (HPMC), hydroxyethylcellulose (HEC), or other mucoadhesive polymers.

The mucoadhesive layer may additionally comprise at least one active agent, a permeation enhancer and/or at least one stimulus-responsive polymer which targets the dosage form to a specific region of the gastro intestinal tract, such as the gastric region or the intestinal region.

The water-insoluble outer layer may comprise a hydrophobic polymer which inhibits the release of the active agent and/or which protects the dosage form from enzymatic or acid degradation in the gastro intestinal tract. The polymer may be a polyamide, ethylcellulose (EC), cellulose acetate phthalate (CAP), a polyacrylonitrile, a polypropylene oxide, a polycaprolactone, or the like. The water-insoluble outer layer may additionally comprise at least one enzyme inhibitor to inhibit enzymatic degradation of the dosage form.

The active agent may be an anti-inflammatory, corticosteroid, antidiarrhoeal, opioid, immunosuppressive, antibiotic, antiemetic, antifungal, antiviral, antimalarial, anti-TB drug, antiretroviral, antihypertensive, protein, peptide, chemotherapeutic, diagnostic agent, probiotic, prebiotic, multivitamin, mineral, trace element, phytonutrient, protein, peptide or the like. More preferably, the active agent may be a narrow absorption window drug, such as acyclovir, bisphosphonates, captopril, furosemide, metformin, gabapentin, levodopa, baclofen or ciprofloxacin, or a combination thereof.

The active agent may be incorporated into the membrane of the intermediate layer. An active agent may also be incorporated into the membrane of the mucoadhesive layer. The active agent may be incorporated into these layers in the form of micro- and/or nanostructures, such as micro- and/or-nanofibres, which may be formed by electrospinning. A cross-linking agent may be used in the electrospinning to strengthen the membranes.

The dosage form may be formulated for oral, vaginal, transdermal, rectal or buccal drug delivery.

According to a second embodiment of the invention there is provided a pharmaceutical dosage form for delivering at least two active agents to different regions of the gastro intestinal tract, the pharmaceutical dosage form comprising two pharmaceutical dosage forms described above, wherein the two dosage forms are connected by a pH polymeric layer which causes the two dosage forms to separate after ingestion.

The one dosage form may be for delivering an active agent to the gastric region of the gastro intestinal tract and the second dosage form may be for delivering an active agent to the intestinal region of the gastro intestinal tract.

According to a third embodiment of the invention, there is provided a method of forming a pharmaceutical dosage form as described above, the method comprising the steps of:

forming a mucoadhesive polymer layer which is capable of adhering to the gastro intestinal tract or buccal mucosa of a human or animal body;

forming an intermediate polymer layer comprising a pharmaceutically active agent, wherein the intermediate layer is formed by electrospinning micro- and/or nano-fibres containing the pharmaceutically active agent onto the mucoadhesive layer, and wherein the micro- or nano-fibres are cross-linked during the electrospinning; and casting a water-insoluble outer layer over the intermediate polymer layer.

According to a third embodiment of the invention, there is provided a method of administering a pharmaceutically active agent to a human or animal, the method comprising the step of administering a dosage forms as described above to the human or animal, wherein the mucoadhesive layer of the dosage form adheres to the wall of the stomach or another region of the gastrointestinal tract, thus preventing premature gastric emptying, duodenal emptying, intestinal emptying, or colonic emptying of the dosage form; and the pharmaceutically active agents are released in a pH-responsive and time dependant manner to the gastrointestinal tract.

DETAILED DESCRIPTION OF THE INVENTION

Figure 1:
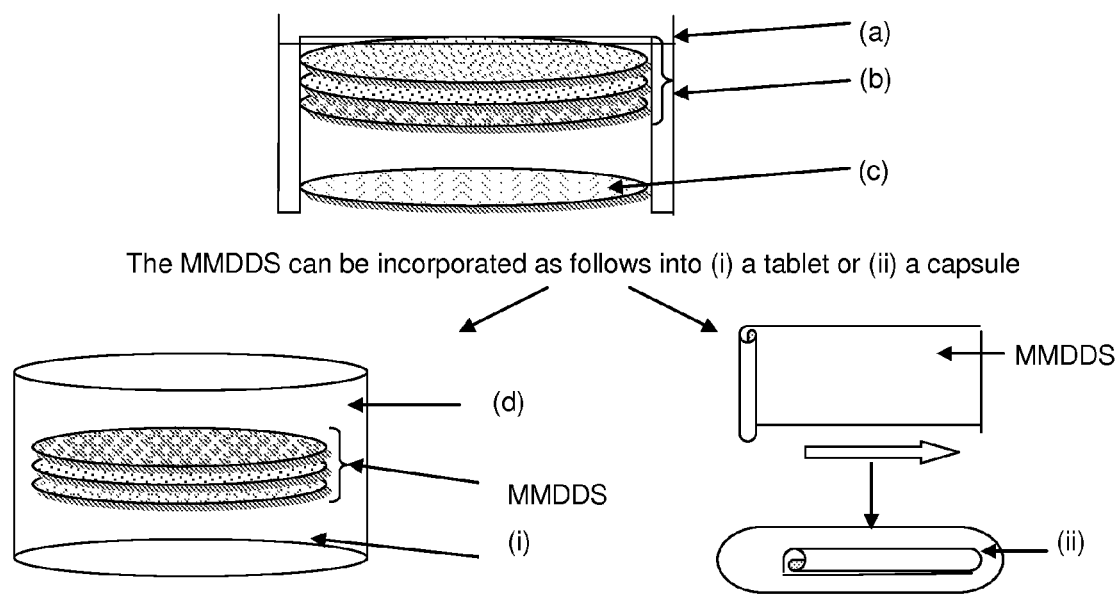
FIG. 1: is a schematic representation of a multilayered mucoadhesive dosage delivery system (MMDDS) according to the present invention, which is incorporated into (i) a tablet matrix or (ii) a capsule.

A pH responsive and mucoadhesive pharmaceutical dosage form for the release of a pharmaceutically active agent is described herein. The dosage form includes a mucoadhesive layer for site-specific mucoadhesion, a water-insoluble outer layer, and an intermediate layer including one or more drugs, pharmaceutically active agents or bioactive agents for site-specific delivery. The different layers perform different functions in order to create a drug delivery system which is able to deliver a drug to a specific site, for a particular period of time and with a specific drug release pattern.

The dosage form can have two or more intermediate layers, each intermediate layer comprising at least one active agent. The mucoadhesive layer can also include one or more active agents. Incorporating multiple active agents into a single dosage form allows for easier doing regimes and is more likely to result in patient compliance.

The dosage form can be formulated for oral or buccal drug delivery, and in particular, is for oral delivery for release of the active agent into the gastro intestinal tract.

Each of the layers is typically in the form of a polymeric membrane. The polymeric membranes can be manufactured from one or more natural and/or synthetic polymers, homo- and/or co-polymers. In particular, the natural polymers can be polysaccharide and/or carbohydrate polymers and the synthetic polymers can be hydrophilic or hydrophobic swellable or erodible polymers, mucoadhesive polymers, and/or stimulus-responsive polymers. The stimulus-responsive polymers are selected so as to target the pharmaceutical dosage form to a specific region of the gastro intestinal tract, such as the gastric region or the intestinal region. Particularly suitable polymers forming the membranes are polyethylene oxide (PEO), polyvinyl alcohol (PVA), ethylcellulose (EC), poly(lactic) co-glycolic acids (PLGA), polylactic acids (PLA), polymethacrylates, polycaprolactones, polyesters and polyamides. The polymer or polymers of at least one of the layers can selected so as to render the pharmaceutical dosage form pH responsive, thus facilitating delivery of the active agent to a specific region. The polymers can be crosslinked so as to retard and prolong the release of the active agent(s) from the dosage form. Crosslinks are introduced into the polymer network by chemically crosslinking with various ions i.e. calcium and zinc ions. The crosslinking agent can be glutaraldehyde (especially gluteraldehyde vapours), formaldehyde and/or an electrolyte or salt selected from the Hofmeister Series of salts. In addition to chemical crosslinking, microwave or UV radiation can also be used to achieve crosslinking of the polymers. The introduced crosslinks form an insoluble meshwork, thus slowing down and prolonging release of the active agent. The polymers are also selected for their ability to entrap and modulate the release of the active agent.

The mucoadhesive layer is typically a polymeric membrane formed from at least one mucoadhesive polymer, such as polyacrylic acid, chitosan, pectin, hydroxypropylcellulose (HPC), hydroxypropylmethylcellulose (HPMC) or hydroxyethylcellulose (HEC). The pharmaceutical dosage form adheres, in use, to the wall of the stomach or another region of the gastrointestinal tract, thus preventing premature gastric emptying, duodenal emptying, intestinal emptying or colonic emptying, depending on the site of adhesion. The increased gastric time will ensure that the full active agent dose is released from the dosage form before being excreted.

As mentioned above, the mucoadhesive layer can include at least one active agent. The mucoadhesive layer can also include a permeation enhancer to improve the bioavailabilities of active agents which have poor oral bioavailabilities. Suitable permeation enhancers are chitosan, sodium laureth sulphate (anionic surfactants), decyltrimethyl ammonium bromide, (cationic surfactants) and the like. The mucoadhesive layer can also include one or more stimulus-responsive polymers which target the dosage form to a specific region of the gastro intestinal tract, such as the gastric region or the intestinal region, and make the active agent(s) available for absorption in a specific site within the gastro intestinal tract, allowing the bioactive agent to act locally at the target site. The mucoadhesive layer enables the dosage form to adhere, in use, to the wall of the stomach or another region of the GIT, thus preventing premature gastric emptying, duodenal emptying, intestinal emptying, or colonic emptying, depending on the site of adhesion.

The water-insoluble outer layer ensures unidirectional release of the active agent and protects active agents which are acid and/or enzyme sensitive, such as proteins and peptides, from acid and/or enzyme degradation within the gastro intestinal tract. As a result of unidirectional release, there will be an increase in local drug concentrations at the site of absorption hence enhancing the absorption efficacy of active agents that have poor oral bioavailabilities. The outer layer can be formed from one or more natural and/or synthetic hydrophobic polymers, such as polyamides, ethylcellulose (EC), cellulose acetate phthalate (CAP), polyacrylonitriles, polypropylene oxides or polycaprolactones. The polymers can be selected so as to render the dosage form pH responsive in use, thus facilitating precise delivery of the active agent(s) to the desired sites of action or absorption, and/or can be selected to adhere within a specific region of the human or animal body in a time-dependent manner, thus facilitating precise delivery of the active agents to the desired site of action or absorption. The outer layer can additionally include one or more enzyme inhibitors.

The active agent can be any suitable drug or bioactive compound, such as an anti-inflammatory, corticosteroid, antidiarrhoeal, opioid, immunosuppressive, antibiotic, antiemetic, antifungal, antiviral, antimalarial, anti-TB drug, antiretroviral, antihypertensive, protein, peptide, chemotherapeutic, diagnostic agent, probiotic, prebiotic, multivitamin, mineral, trace element, phytonutrient, protein, peptide or the like. In particular, the active agent can be a drug with poor aqueous solubility or a narrow absorption window drug, such as acyclovir, bisphosphonates, captopril, furosemide, metformin, gabapentin, levodopa, baclofen or ciprofloxacin, or the like, or a combination thereof.

The active agent can be incorporated into the membrane of the intermediate layer. An active agent can also be incorporated into the membrane of the mucoadhesive layer. The polymers used to form the layered membranes in which the active agent is included are typically selected for their ability to entrap and modulate the release of the active agent. The release of the active agent from the intermediate layer depends on the crosslinking agent employed, the degree of ionization of the crosslinking agent, the solution pH, the ratio of dry polymer to pepsin, and the degree of crosslinking.

The active agent can be incorporated into the membranes in the form of micro- and/or nanostructures, such as micro- and/or nanofibers, which are typically formed by electrospinning. Electrospinning is an efficient membrane fabrication process that can be utilised to assemble fibrous polymeric membranes composed of fiber diameters ranging from nanometers to micrometers. The electrostatic processing method uses a high-voltage electric field to inject a charge of a certain polarity into the polymeric solution/melt which is accelerated toward a collecting surface of opposite polarity, thus forming solid fibres. Electrospun fibrous matrices possess a three dimensional porous structure with a relatively large surface area. Good fibre formation requires optimization of the solution parameters and electrospinning configuration. Controlling parameters during electrospinning influences drug release patterns from the membranous matrices. In this manner, electrospun membranous matrices can be customized to achieve desired drug release patterns. The polymers for electrospinning, such as polyanilines, polyacetylenes, polypyrroles or the like, together with the active agent(s), solvents and excipients are combined in a solution, suspension, emulsion or melt form and a voltage of from about 1-20 kV can be applied to the polymeric solution, suspension, emulsion or melt form. The active agent can be incorporated by direct dissolution, suspended or in an emulsion form. Suitable solvents for preparing the electrospinning solutions include water and organic and inorganic solvents. Typical excipients are plasticizers, surfactants and/or antifoaming agents. A catalyst can also be used, including but not limited to, acids such as hydrochloric acid, acetic acid and formic acid.

FIG. 1 represents a) a water insoluble polymeric layer coating a multi-component membrane drug delivery system (MMDDS) comprised of poorly water soluble polymers, as an example of a dosage system of the present invention. Incorporation of enzyme inhibitors such as pepstatin (for pepsin) within the coating will prevent enzyme degradation of the MMDDS in the gastro intestinal tract (GIT); b) electrospun fibrous layer/s containing one or more drugs; and c) a film-casted mucoadhesive layer that allows the membrane system to adhere to the GIT mucosa. Permeation enhancers such as chitosan are incorporated into this layer to further improve the oral bioavailability of orally less efficient drugs. pH-responsive polymers within this layer targets the system to a specific area of the GIT. The MMDDS can be incorporated into (i) a tablet with (d) representing a surrounding tablet matrix comprising various pH responsive polymers used to protect and target the MMDDS; or (ii) a capsule formed by rolling of the MMDDS.

Figure 2:
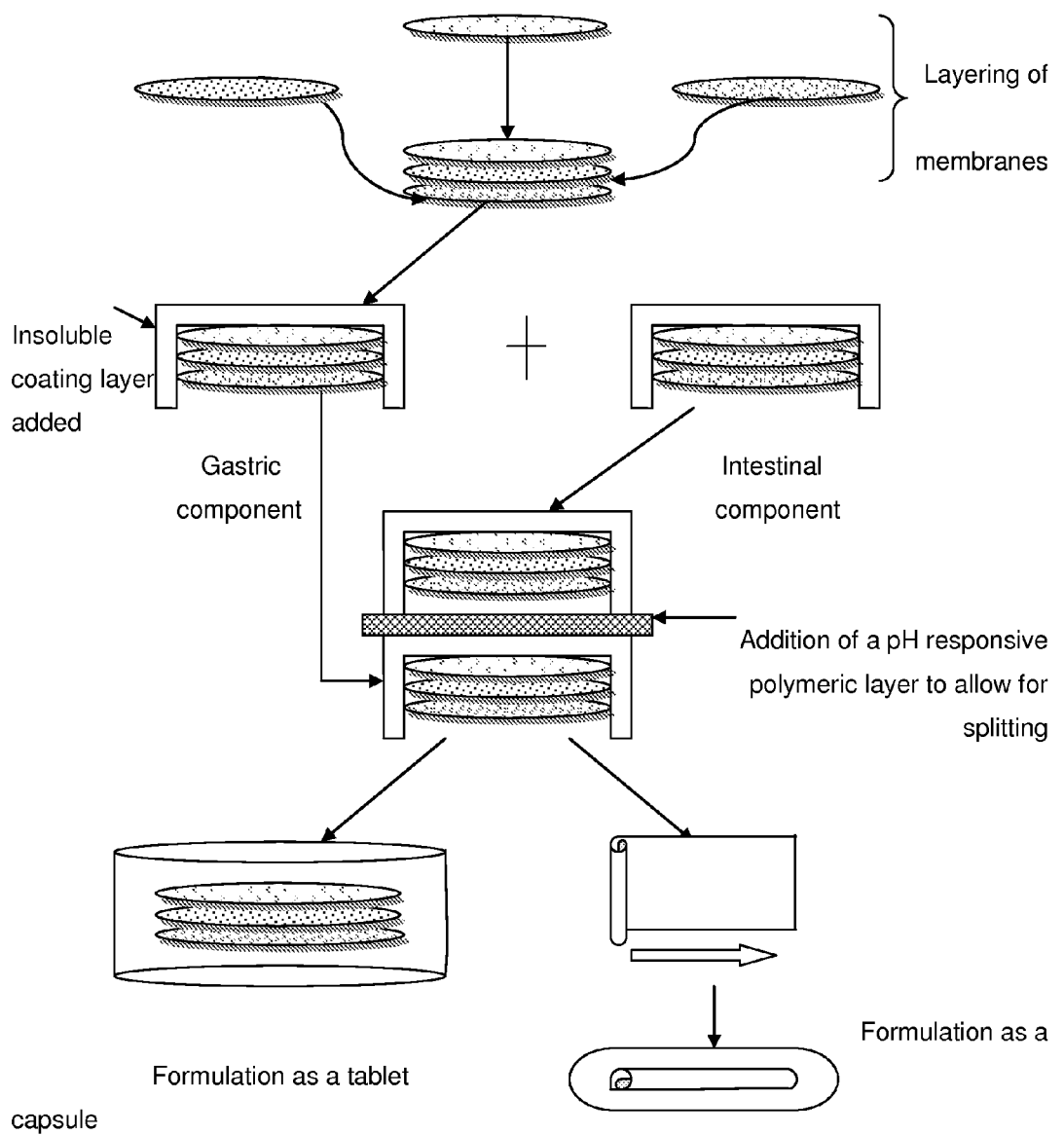
FIG. 2: is a schematic representation depicting the formulation of a double dosage form of the invention.

Two pharmaceutical dosage forms described above can be combined by joining them together with a pH polymeric layer which causes the two dosage forms to separate after ingestion. For example, the one dosage form may be for delivering an active agent to the gastric region of the gastro intestinal tract and the second dosage form may be for delivering an active agent to the intestinal region of the gastro intestinal tract (FIG. 2).

Manipulating the mucoadhesive layer to be pH-responsive will allow these systems to prolong drug release at the specific site of absorption, thus maintaining steady plasma concentrations of the drug. This MMDDS will include both a gastric and an intestinal component which allows for site-specific drug delivery.

The release of the active agents from the intermediate electrospun layer is governed by several factors, including the crosslinking agent employed, the degree of ionization of the crosslinking agent, the solution pH, the ratio of dry polymer to crosslinking agent, and the degree of crosslinking.

The invention will now be described in more detail by way of the following non-limiting examples.

EXAMPLES

Materials

Poly(acrylic acid) (PAA), pectin (PEC) classic Cu701 (Herbstreith & Fox K G), PEC classic AM901, chitosan (CHT), poly(vinyl alcohol) (PVA) (Mw=88000 g/mol), PVA (Mw=13000-28000 g/mol and Mw-124000-186000 g/mol), poly(ethylene oxide) (PEO) WSR 205 and 301 and hydroxypropylcellulose (HPC) were polymers utilized in this study. Diphenhydramine (DPH) was used as the model drug. Hexamethylenediamine (HMD), sodium hydroxide (NaOH), hexane, cyclohexane and sebacoyl chloride (SC) were utilized to synthesize polyamide 6,10. An antifoaming agent, silicone, was incorporated to prevent air bubble formation in the membranes. Glycerine was incorporated as a plasticizer. Dialysis flat-sheet membrane Mw=12000-14000 g/mol (Spectrum Laboratories), was utilised as a simulated gastric membrane. Solvents include deionised water, 0.1M acetic acid and 85% formic acid.

Membrane Formation Methods

Figure 3:
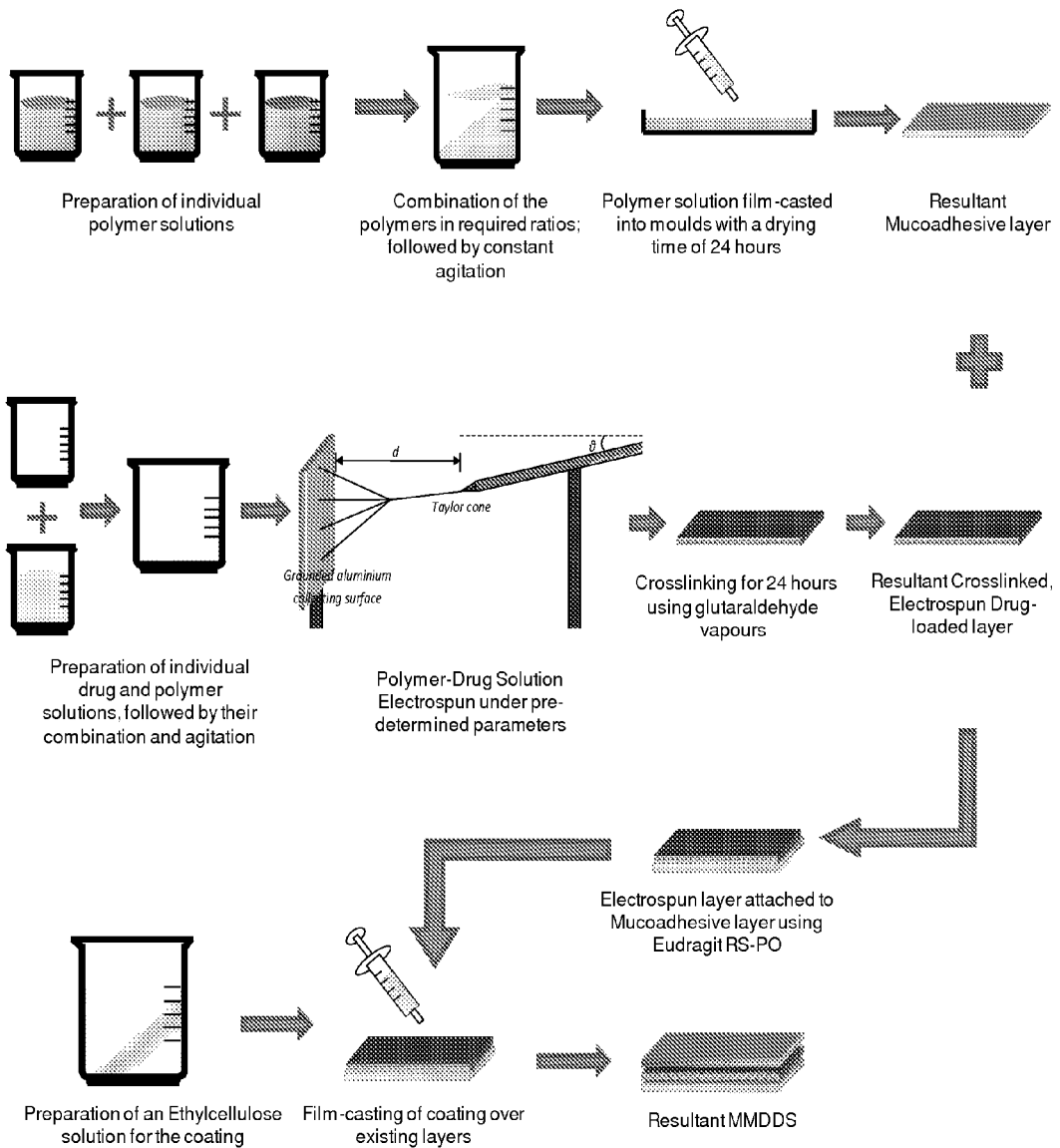
FIG. 3: is a schematic representation showing formulation of the MMDDS.

A multilayer membrane drug delivery system (MMDDS), consisting of a mucoadhesive layer, drug-containing layer and water insoluble coat, was prepared. The MMDDS was assembled as illustrated in FIG. 3.

Mucoadhesive Layer

Figure 4:
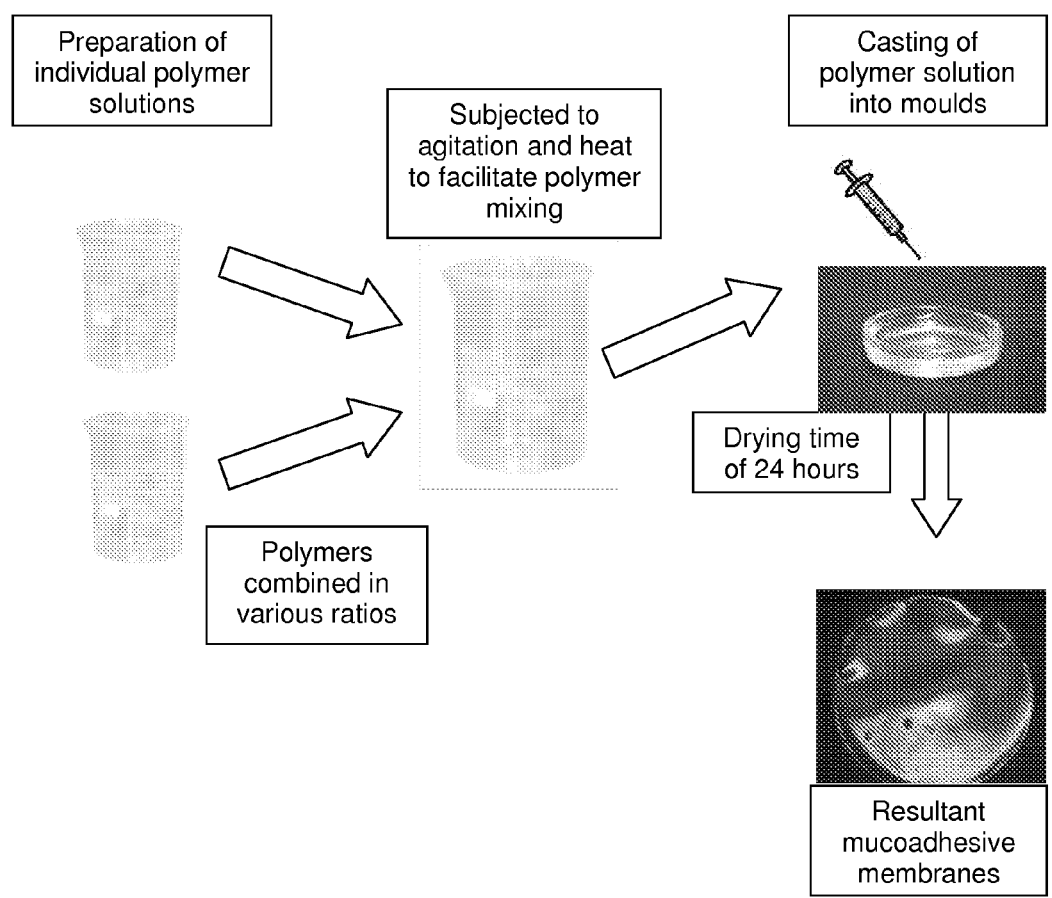
FIG. 4: shows a method for preparing a mucoadhesive membrane of the dosage form.

Combinations of PAA with PEC Classic CU 701 or CHT were investigated for the mucoadhesive layer. The polymers were dissolved in their respective solvents and subsequently blended in various ratios as illustrated in Table 1. Mucoadhesive membranes were then cast in moulds and allowed to dry for a period of 24 hours (FIG. 4).

TABLE 1

Ratios of polymer blends utilised to prepare the mucoadhesive layer

| Formulation | Ratio Polymer A | Ratio Polymer B |
|---|---|---|
| In pH 6.8 | Chitosan (2%) | PAA (4%) |
| 1 | 1 | 1 |
| 2 | 1 | 0 |
| 3 | 1 | 2 |

TABLE 1-continued

Ratios of polymer blends utilised to prepare the mucoadhesive layer

| Formulation | Ratio Polymer A | Ratio Polymer B |
|---|---|---|
| 4 | 2 | 1 |
| 5 | 1 | 4 |
| In pH 1.2 | Pectin (4%) | PAA (4%) |
| 6 | 1 | 1 |
| 7 | 1 | 0 |
| 8 | 1 | 2 |
| 9 | 2 | 1 |
| 10 | 1 | 4 |
| 11 | 4 | 1 |

Figure 5:
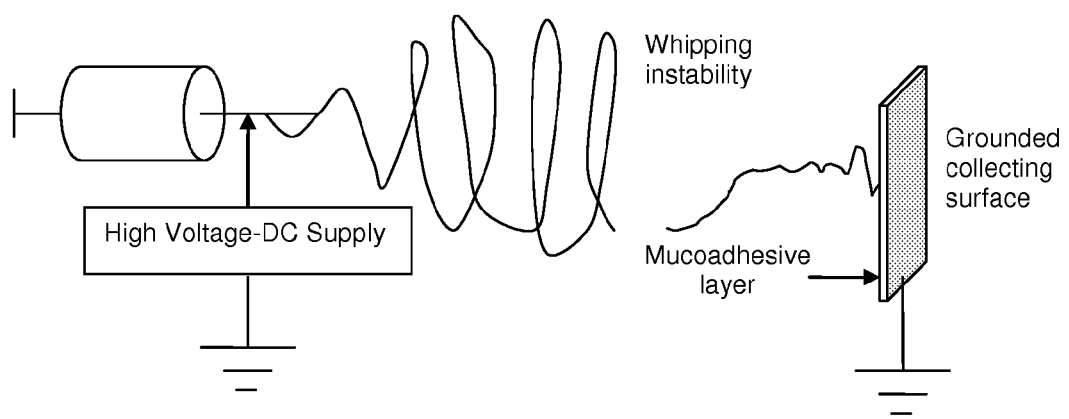
FIG. 5: is a schematic representation of the electrospinning procedure used in making the dosage form.
Figure 6:
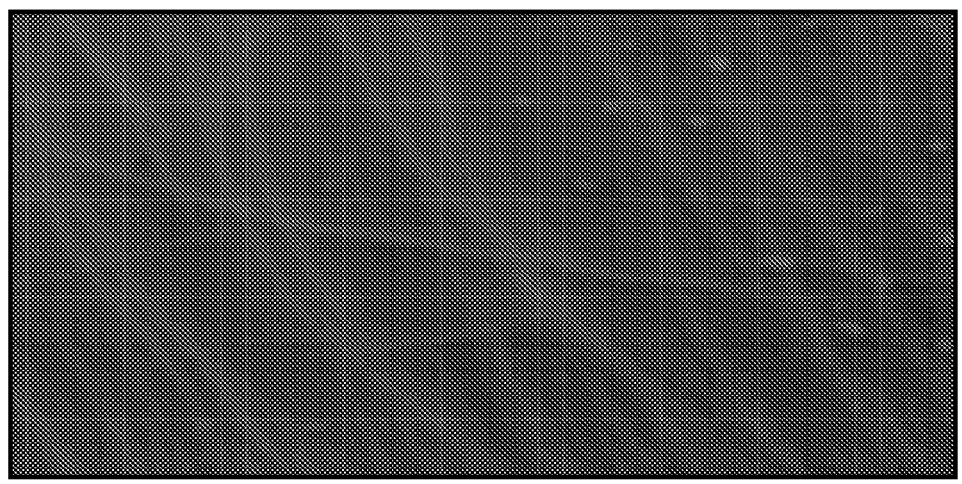
FIG. 6: shows a micrograph illustrating typical electrospun PVA fibres (drug loaded).

Drug Loaded Electrospun Fibre Layer (i) Polymers including Poly(vinyl alcohol) (PVA) Mw (13000-23000) and Mw (88000), PVA 87-89% hydrolyzed (Average Mw: 146000-186000), and Poly(ethylene oxide) (PEO) WSR 205 and 301, were investigated for electrospun membranes. 10% and 30% solutions of PVA and 3% solutions of PEO were prepared. Preliminary electrospinning studies resulted in poor membrane formation, and thus a plasticizer, glycerine, was incorporated into the electrospinning solution on a 2:1 ratio of polymer:plasticizer. In addition, polymer solvents utilised were varied in order to determine the effect of solvent on membrane formation. Solvents including water and a water:propan-2-ol ratio were investigated. Drug loading was attempted by dissolving a model drug, Diphenhydramine HCl (DPH) in the polymeric solution prior to electrospinning. Polymer solutions were subject to a predetermined voltage and allowed to electrospin for a time period sufficient to produce acceptable membranes. Fibres were spun directly onto the mucoadhesive layer as illustrated in FIG. 5. FIG. 6 illustrates the typical diameters of electrospun PVA fibres, with diameters ranging from 30-160 μm.

Figure 7:
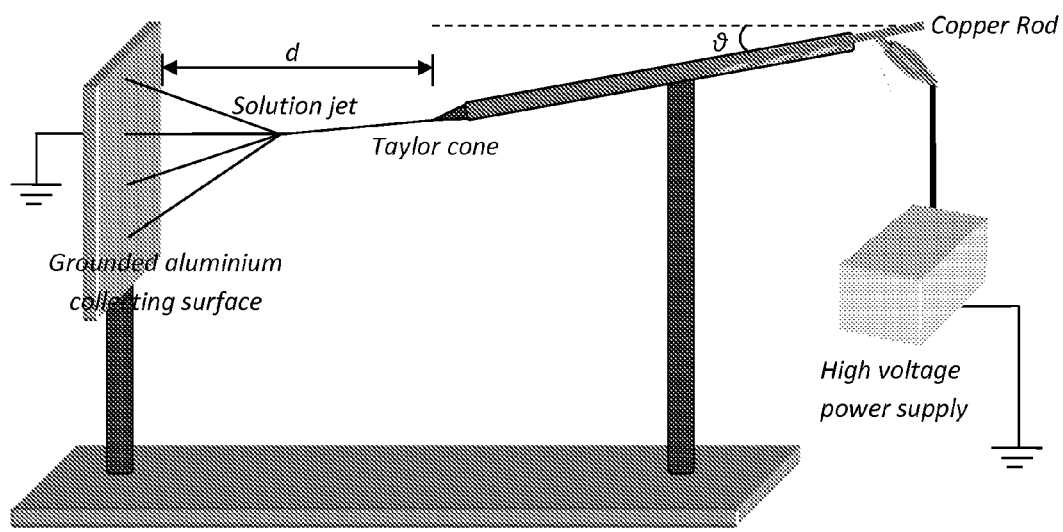
FIG. 7: is a schematic illustration of the horizontal electrospinning process.

(ii) Drug solutions were prepared at ambient room conditions in their respective solvents at concentrations illustrated in Table 2. Once a clear drug solution was obtained, the antioxidant (ascorbic acid) was added to the solution to prevent any degradation of the drug. The antioxidant-drug solution was then further agitated to produce a homogenous solution. Silicone/Tween 80 was then added to the solution, followed by addition of the polymer. Once a homogenous solution was obtained, electrospinning was carried out as follows:

The electrospinning setup, as illustrated in FIG. 7, involved applying 20 kV, supplied by a Glassman High Voltage, INC (High Bridge, N.J., USA) to the drug-polymer solutions in 5 mL Goldline glass pipettes via a copper rod. The pipettes containing the drug-polymer solutions were mounted at distances of 21-28 cm from the collecting surface. The solution was fed through a capillary size of ±1.2 mm from a horizontal electrospinning setup, with the capillary being angled at 10°-11.5° from the horizontal surface. The electrospun fibres were collected on an aluminium sheet connected to a grounded counter electrode. Electrospinning was carried out at ambient room conditions for periods ranging between 5-8 hours. The fibres were carefully removed from the aluminum collector and stored in air-tight containers, in the presence of a desiccant, until further processing was carried out.

TABLE 2

Electrospinning parameters of INH- and RIF-loaded nanofibres

| Parameters | RIF-loaded nanofibres | INH-loaded nanofibres |
|---|---|---|
| Solution Parameters | | |
| PVA Concentration | 8% w/v | 10% w/v |
| Solvent for PVA solution | Double deionised water | Double deionised water |
| Drug concentration | 2% w/v | 2% w/v |
| Solvent for drug solution | Weak HCl solution | Double deionised water |
| Surfactant | Tween 80 at 5% w/v | None added |
| Antioxidant | Ascorbic acid at 1% w/v | None added |
| Anti-foaming agent | None added | Silicone anti-foaming agent (1 drop per 50 mL) |
| Electrospinning Parameters | | |
| Voltage Supplied | 20 kV | 20 kV |
| Distance between capillary tip and collecting surface (d) | 28 cm | 21-24 cm |
| Capillary size | 1.2 mm | 1.2 mm |
| Capillary angle (θ) | 11.5° | 10° |

Crosslinking of Drug-Loaded PVA Nanofibres

Figure 8:
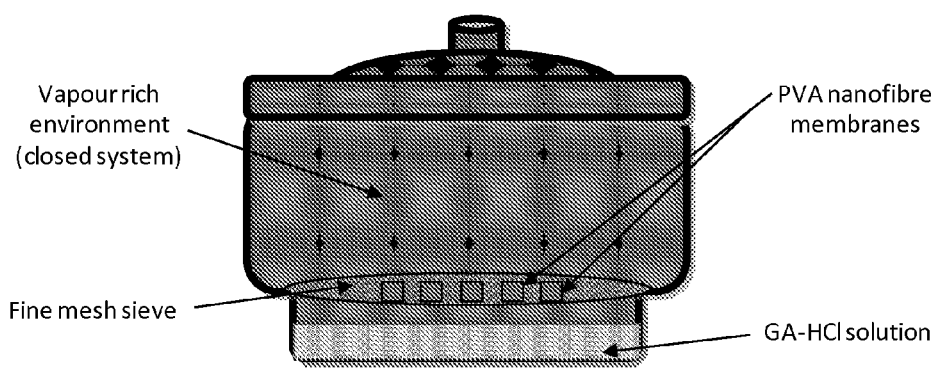
FIG. 8: is a schematic illustration of the crosslinking procedure of PVA nanofibre membranes.

Crosslinking was carried out in the presence of GA vapors. HCl (32% w/v), acting as a catalyst, was added to the GA solution on a 3:1 ratio of GA:HCl. The GA-HCl was thereafter placed in the lower portion of desiccant jars and accurately weighed samples of drug-loaded PVA nanofibers were suspended over the solution using a fine mesh sieve. Formulations were crosslinked according to parameters illustrated in Table 3. The system was closed to impart a vapour-rich environment as illustrated in FIG. 8. Drug-loaded membranes were allowed to crosslink in the vapour-rich environment for periods ranging from 6 to 24 hours at ambient room conditions, and thereafter stored in airtight containers with the presence of a desiccant until further testing was performed.

TABLE 3

Crosslinking variables of non-drug and drug-loaded PVA nanofibres

| Formulation | Drug Concentration | PVA Concentration | Concentration GA:HCl (mL) | Time (hours) |
|---|---|---|---|---|
| 1 | — | 10% w/v | — | — |
| 2 | INH: 2% w/v | 10% w/v | — | — |
| 3 | INH: 2% w/v | 10% w/v | 15:5 | 24 |
| 4 | INH: 2% w/v | 10% w/v | 30:10 | 12 |
| 5 | INH: 2% w/v | 10% w/v | 60:15 | 6 |
| 6 | — | 8% w/v | — | — |
| 7 | RIF: 2% w/v | 8% w/v | — | — |
| 8 | RIF: 2% w/v | 8% w/v | 15:5 | 24 |
| 9 | RIF: 2% w/v | 8% w/v | 30:10 | 12 |
| 10 | RIF: 2% w/v | 8% w/ | 60:15 | 6 |

Polymeric Coating

Slow release polyamide 6, 10 was synthesised to develop the coating layer of the MMDDS.

Preparation of Polyamide 6, 10

Two separate, manipulated, solutions were mixed together to form Polyamide 6, 10. These comprised an aqueous (polar) solution containing 10 mls De-ionized Water (DW) to which 1.75 g of Hexamethylenediamine (HMD) and 0.1 g Sodium Hydroxide (NaOH) were added. A Non-Aqueous (non-polar) solution comprising equal quantities of Hexane (HEX) and Cyclohexane (C-HXN) was prepared. 0.63 mls of Sebacoyl Chloride (SC) was added to the non-aqueous phase. The non-aqueous mixture (HEX, C-HXN, SC) was then gradually added to the aqueous solution (DW, HMD, NaOH) and the final mixture stirred with a glass rod. A white gel-like mass formed and stirring continued until this substance could no longer absorb solvent. The polymer was rinsed with 200 ml of distilled water three consecutive times and then placed on filter paper and dried at 45° C.

Preparation of the Polymeric Coating

A polyamide 6, 10 solution was prepared using formic acid (85%) as solvent. The resultant solution was then film-cast and allowed to dry for 48 hours (FIG. 3).

Mucoadhesion Properties of the MMDDS

In order to evaluate the mucoadhesion of the drug delivery system of the invention, the tensile force required to separate the hydrated membrane from a portion of simulated gastric membrane was determined, using Texture Analyser TA.XTplus (Stable Microsystems, England). Portions of Dialysis Flat Sheet Membranes Mw 12000-14000 were secured to the probe, while a hydrated section of the mucoadhesive membrane was secured to the stand. Polymeric membranes were hydrated with Simulated Gastric Fluid (SGF) (pH 1.2) and Simulated Intestinal Fluid (SIF) (pH 6.8) over a period of 12 hours and tested for their mucoadhesive properties. The probe was lowered so that it came into contact with the simulated gastric membrane mount and the force required to remove the polymeric membrane was determined from the force: distance curve. The experiment was conducted in triplicate in order to ensure the accuracy of results. Membranes were subject to parameters described in in vitro drug release.

Figure 9:
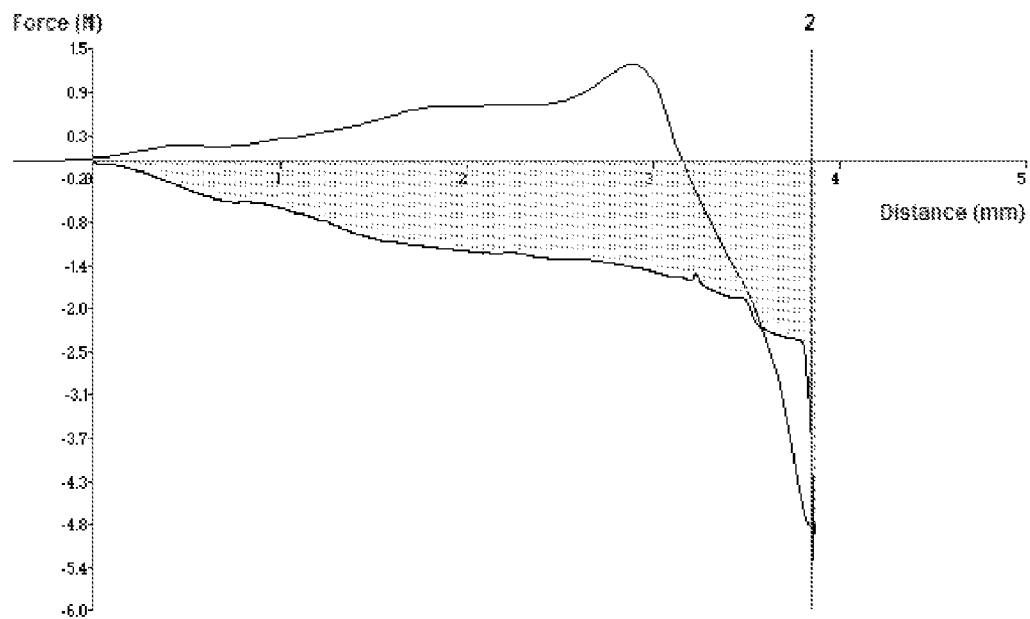
FIG. 9: shows a typical force: distance curve illustrating the maximum force required to detach the mucoadhesive membrane (formulation 8) from simulated gastric membranes.
Figure 10:
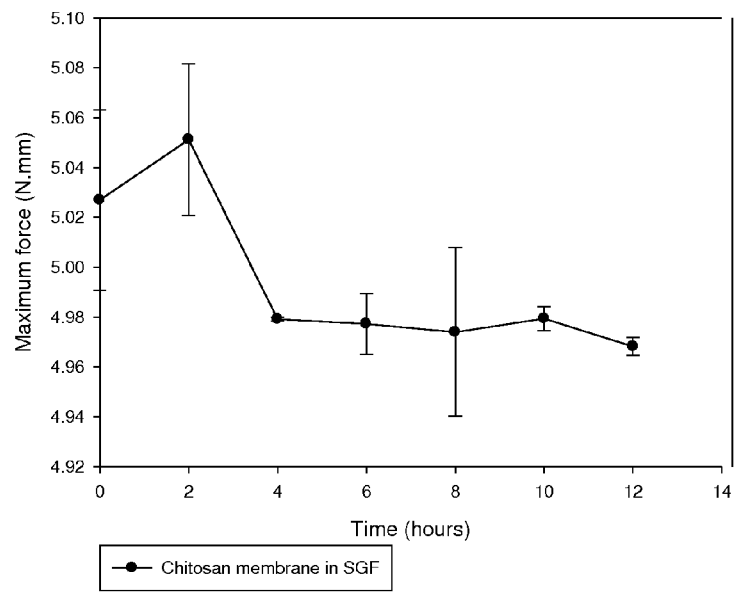
FIG. 10: is a graph showing the force required to detach the mucoadhesive membrane from simulated gastric membranes in simulated gastric fluid (SGF) over a 12 hour period.
Figure 11:
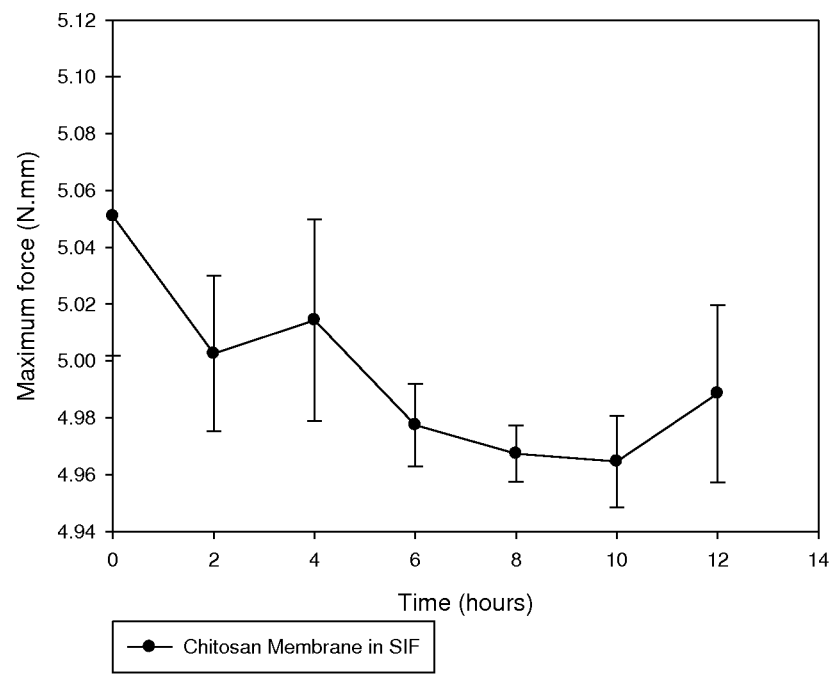
FIG. 11: is a graph showing the force required to detach the mucoadhesive membrane from simulated gastric membranes in simulated intestinal fluid (SIF) over a 12 hour period.

FIG. 9 shows a typical force:distance curve obtained from the 12 hour mucoadhesive study. The maximum force required to detach the polymeric membrane from the simulated gastric membrane can be related to the mucoadhesive properties of the membrane, where the higher the force is, the stronger the mucoadhesive properties of the polymeric membrane. Samples were analysed for their mucoadhesive properties at 0, 2, 4, 6, 8, 10 and 12 hour intervals. All formulations were subject to the 12 hour study. However, formulations 1 and 3-5 disintegrated in SGF within 2 hours and thus these samples were only analysed in SIF. Formulations 6-11 disintegrated in SIF within 2 hours and thus these samples were only analysed in SGF. Formulation 2 (2% Chitosan membrane) did not disintegrate over the 12 hour period and is graphically represented in FIGS. 10 and 11. The mucoadhesion of the chitosan membrane remained consistent (4.96-5.06 N·mm) over the 12 hour period in both SGF and SIF. Formulation 8 showed the highest mucoadhesion property at time=0 hours of 5.5570 N·mm (Table 4).

TABLE 4

Maximum Force required to detach mucoadhesive membranes from simulated gastric membranes

| Formulation | Ratio Polymer A | Ratio Polymer B | Maximum Force (N · mm) |
|---|---|---|---|
| In pH 6.8 | Chitosan (2%) | PAA (4%) | |
| 1 | 1 | 1 | 5.06535 |
| 2 | 1 | 0 | 5.0595 |
| 3 | 1 | 2 | 4.7087 |
| 4 | 2 | 1 | 5.0228 |
| 5 | 1 | 4 | 5.0457 |

TABLE 4-continued

Maximum Force required to detach mucoadhesive membranes from simulated gastric membranes

| Formulation | Ratio Polymer A | Ratio Polymer B | Maximum Force (N · mm) |
|---|---|---|---|
| In pH 1.2 | Pectin (4%) | PAA (4%) | |
| 6 | 1 | 1 | 5.0652 |
| 7 | 1 | 0 | 5.3615 |
| 8 | 1 | 2 | 5.5544 |
| 9 | 2 | 1 | 5.26225 |
| 10 | 1 | 4 | 5.33055 |
| 11 | 4 | 1 | 5.14265 |

Nanofibre Drug Entrapment Efficiency

Drug-loading was attempted by dissolving the model drug, diphenhydramine HCl (DPH), in the polymeric solution prior to electrospinning. 1% (w/v) DPH was dissolved in the polymeric solutions and then subjected to electrospinning. Known masses of the polymeric nanofibers were dissolved in buffer and quantified using a standard curve generated for DPH. The test was performed in triplicate.

In order to determine the DEE of RIF- and INH-loaded PVA nanofibers, accurately weighed samples of RIF- and INH-loaded nanofibers were dissolved in 100 mLs of phosphate buffered saline (PBS) (37° C.) at pH 1.2 and 6.8 respectively. The drug content was analyzed by UV spectrophotometry (Lambda 25, UV/VIS Spectrometer, PerkinElmer®, Waltham, Mass., USA) (parameters illustrated in Table 5) and computed from a standard linear curve of the drug in PBS. All tests were performed in triplicate (N=3) and presence of the polymer and the antioxidant, ascorbic acid, was taken into account. Equation 1 was used to compute the DEE, where the theoretical drug (mg) in the formulation was determined as a function of the fibre weight.

$$\% \; DEE = \frac{D_a}{D_t} \times 100 \quad \text{Equation 1}$$

where
% DEE=Percentage of drug entrapped
$D_a$=Actual drug quantity (mg) measured by UV spectrophotometry
$D_t$=Theoretical drug (mg) added to the formulation.

TABLE 5

Parameters employed to determine DEE of RIF and INH-loaded PVA nanofibres

| Drug | RIF | INH |
|---|---|---|
| PBS | pH 1.2; 37° C. | pH 6.8; 37° C. |
| Wavelength | 237 nm | 263 nm |
| Standard linear curve | RIF in PBS (pH 1.2; 37° C.) | INH in PBS (pH 6.8; 37° C.) |
| $R^2$ value | $R^2 = 0.9996$ | $R^2 = 1$ |

Figure 12:
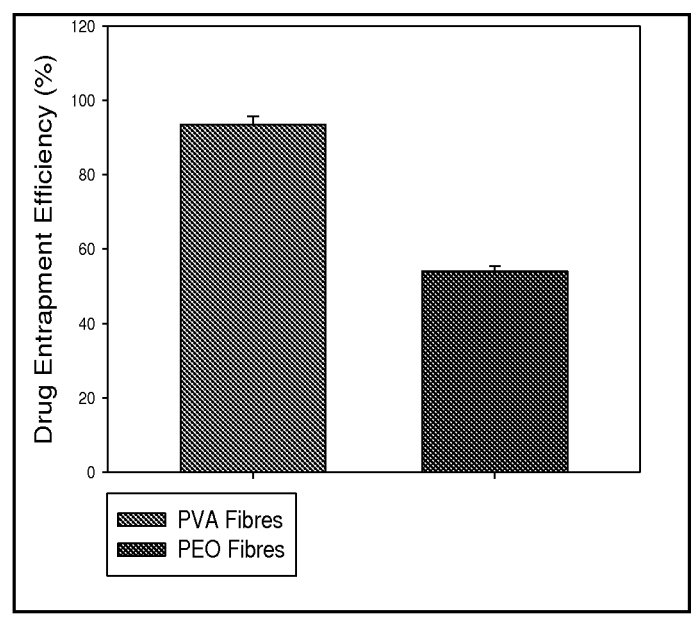
FIG. 12: is a graph showing % drug entrapment efficiency (DEE) of diphenhydramine (DPH) for poly(vinyl alcohol (PVA) and poly(ethylene oxide (PEO) fibres.

Studies indicated that the DEE value was significantly higher with PVA as compared to PEO (93.5% vs. 54% for PVA and PEO, respectively), thus indicating that PVA possessed a greater potential for entrapping DPH due to its hydrophilic nature (FIG. 12).

Figure 13:
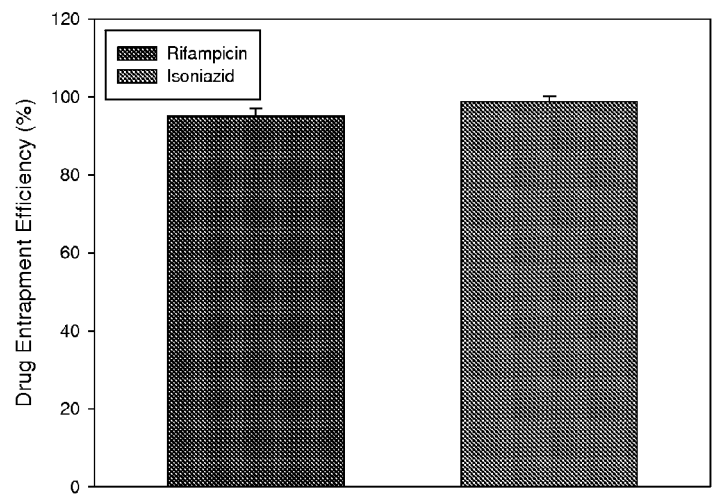
FIG. 13: shows the drug entrapment efficiency of Rifampicin- and Isoniazid-loaded nanofibres.

A drug entrapment value of 95.07±1.988% and 98.77±1.384% was calculated for the RIF-loaded and INH-loaded PVA nanofibers, respectively (FIG. 13). DEE results indicate that drug-loading of nanofibers as opposed to nanoparticles is significantly higher. This can be attributed to the method of nanofiber formulation, where electrospinning of the drug-polymer solution allows for the drug to become embedded in the nanofibers. As RIF and INH have differing solubilities, it should be noted that DEE of PVA nanofibers does not depend on the solubility of the drugs, but rather through the parameters used during electrospinning.

In Vitro Drug Release Studies

In vitro drug release studies were performed using the USP 25 rotating paddle method in a Caleva Dissolution Apparatus (model 7ST; G.B., Caleva Ltd., Dorset, UK). The MMDDS was exposed to 900 mls of Simulated Gastric or Intestinal fluid. Membranes were subjected to the paddle method of in vitro drug release studies at 50 rpms, for 12 hours in pH 1.2 for the gastric component and pH 6.8 for the intestinal component at 37° C.±0.5. Samples were obtained on an hourly basis and analysed by UV spectroscopy (SPECORD 40, Jena, Germany) in order to determine the drug absorbance and subsequently drug release.

Nanofibrous matrices dissolve instantaneously upon contact with a dissolution medium. As a result, drug release from the fibrous matrices is immediate. Vapor-induced crosslinking of the PVA fibres imparted water-insoluble properties in the fibrous network, resulting in the potential to enhance prolonged drug release. Drug release from nanofibrous membranes is a two-step mechanism, starting with an initial desorption of drugs from the fiber surface with fast diffusion into the aqueous phase, followed by solid-state diffusion of drug from within the solid nanofibers (Leung and Ko, 2011).

The burst release of INH and RIF, demonstrated in all formulations investigated for drug release, can be attributed to the initial desorption and fast diffusion of drug from the nanofiber surface into the dissolution medium. This is followed by solid-state diffusion of drugs through the solid PVA nanofibers, which occurs at a relatively reduced rate, accounting for the slower rate of drug release after 4 hours. INH-loaded nanofibrous membranes demonstrated slower drug release over 12 hours in formulations crosslinked for a longer duration (Formulation 3) as opposed to those crosslinked for shorter durations (Formulation 4; 5). Formulation 3, the INH-loaded nanofibers crosslinked in the presence of 15 mL GA for 24 hours, depicts the most desired drug release kinetics of a pseudo-zero order type release kinetics, with 81.11±2.35% being released over 12 hours. Although the quantity of crosslinker increased in formulations 3-5, the decrease in crosslinking time was considerable to cause relatively faster drug release in Formulations 4 and 5 as opposed for Formulation 1.

Figure 14:
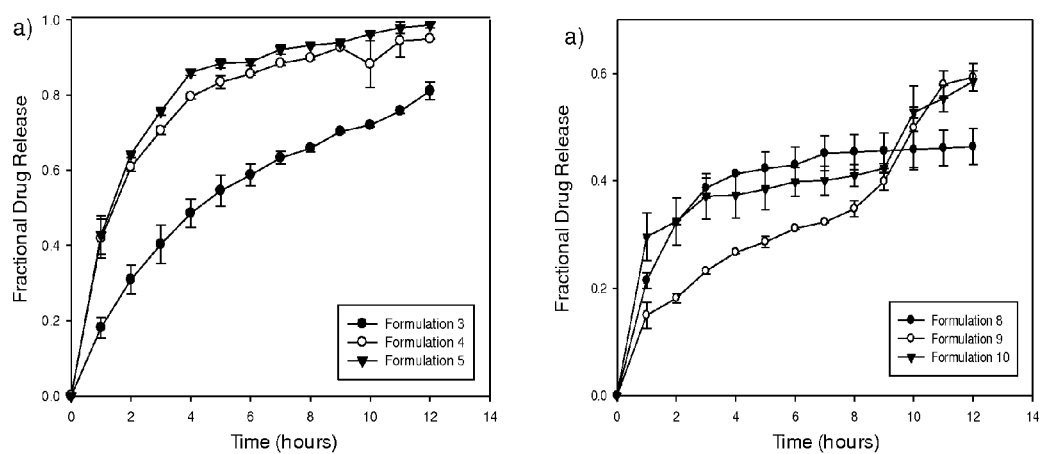
FIG. 14: shows drug release profiles of a) formulations 3-5 in pH 6.8±0.1 at 37±0.5° C. and b) formulations 8-10 in pH 1.20.1 at 37±0.5° C.

When considering RIF-loaded formulations, Formulation 9 demonstrated optimal drug release kinetics with 59.31±2.57% being release over 12 hours in the most controlled manner. The variations in the drug release between the INH-loaded and RIF-loaded nanofibrous membranes can be attributed to the hydrophilicity of the respective drug molecules. INH, a hydrophilic drug molecule, required longer crosslinking periods as compared to RIF, which has a hydrophobic nature, to obtain prolonged drug release characteristics. The hydrophobic nature of RIF ultimately resulted in slower drug release of RIF-loaded nanofibrous membranes than INH-loaded formulations of the same crosslinking quantity and time, depicted in FIG. 14 where Formulation 3 released 81.11±2.35% of INH over 12 hours as opposed to Formulation 8 where 46.34±3.35% of RIF was released over 12 hours.

Rheological Characteristics of the Non-Drug Loaded and Drug Loaded Polymeric Solutions Employed in Electrospinning The rheological characteristics, and in particular the viscosity, of polymeric solutions determines whether the solution can be electrospun, and further influences the fiber morphology (such as size) and quality once electrospun. Several studies have demonstrated that polymeric solutions can be electrospun only within an optimal range of polymer concentrations or solution viscosity. If a polymer solution is too dilute, the polymeric fiber breaks up into droplets before reaching the collecting surface. When solutions are too concentrated, fibers are unable to form due to very high viscosities [11; 18]. Increasing the polymer concentrations within said range causes and increase in the diameter of the nanofibers formed [11].

The respective viscosities, determined through rheological analysis of the drug-loaded and non-drug loaded polymeric solutions, are listed in Table 6. As illustrated in the table, addition of RIF causes a drastic increase in the viscosity of the 8% w/v PVA solution. During preliminary investigations, when RIF was added to a 10% w/v solution, the viscosity increase fell outside the optimal viscosity range for electrospinning of PVA solutions. This necessitated lowering the PVA concentration in RIF-loaded solutions from 10% w/v PVA to 8% w/v PVA solution, which had better electrospinnable characteristics. In addition, incorporation of Tween 80 to the RIF-loaded PVA solutions caused a further decrease in the viscosity, further improving the electrospinning characteristics of the solution. INH addition demonstrated a minor increase in the polymer concentration, which had no drastic changes in the morphology or diameters of the fibers formed.

TABLE 6

Effect of drug and/or excipient addition of the viscosity of PVA solutions employed during electrospinning

| Solution Parameters | Viscosity at shear rate of 100/s (mPas) |
| --- | --- |
| 10% w/v PVA | 830.53 ± 26.41 |
| 10% w/v PVA + 2% w/v INH | 945.29 ± 5.62 |
| 8% w/v PVA | 443.14 ± 13.90 |
| 8% w/v PVA + 2% w/v RIF | 707.27 ± 13.60 |
| 8% w/v PVA; 2% w/v RIF + Tween 80 | 647.92 ± 10.31 |

Surface Morphology and Network Density of the Nanofibrous Membranous System

Figure 15:
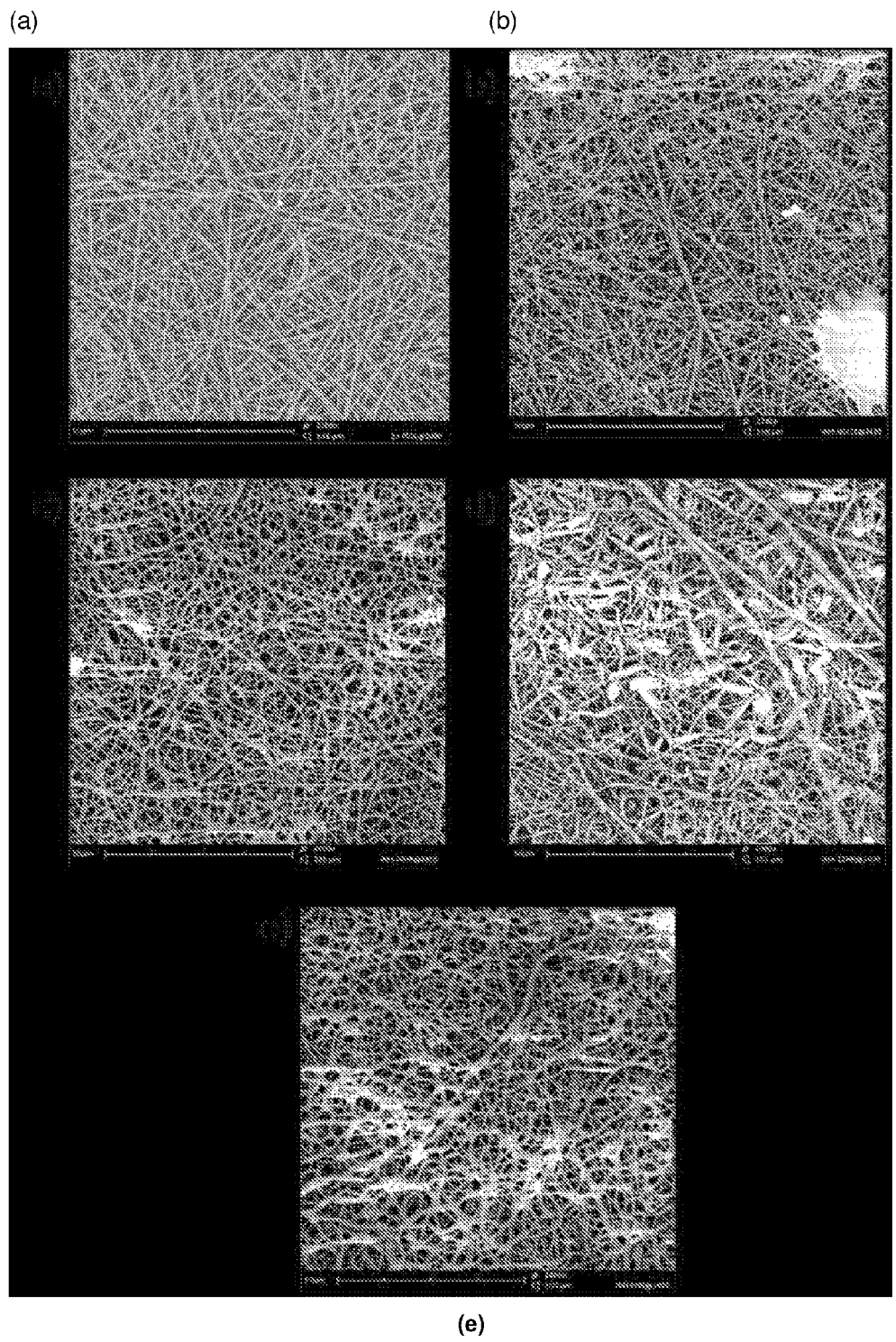
FIG. 15: shows scanning electron micrographs of a) formulation 1, b) formulation 2, c) formulation 3; d) formulation 4 and e) formulation 5.

Scanning electron microscopic evaluation revealed solid, uniform, cylindrical nanofibers of a non-porous surface with random orientation. The absence of pores on the surface of the nanofibers is principally dependant on the type of solvent used, water, which has a relatively low volatility, and thus prevents the formation of pores. The absence of surface pores on the nanofibers prevented an even higher burst release rate of drug which is characteristic of all electrospun nanofibers [17]. As discussed previously, the notion of increasing the polymer concentration causes an increase in fiber diameter, is clearly seen when comparing FIG. 15a and FIG. 16a. When increasing the polymer concentrations from 8% w/v (FIG. 16a) to 10% w/v PVA (FIG. 15a) an increase in the fiber diameter from 297.5±29.47 nm to 345.00±30.41 nm was demonstrated.

Figure 16:
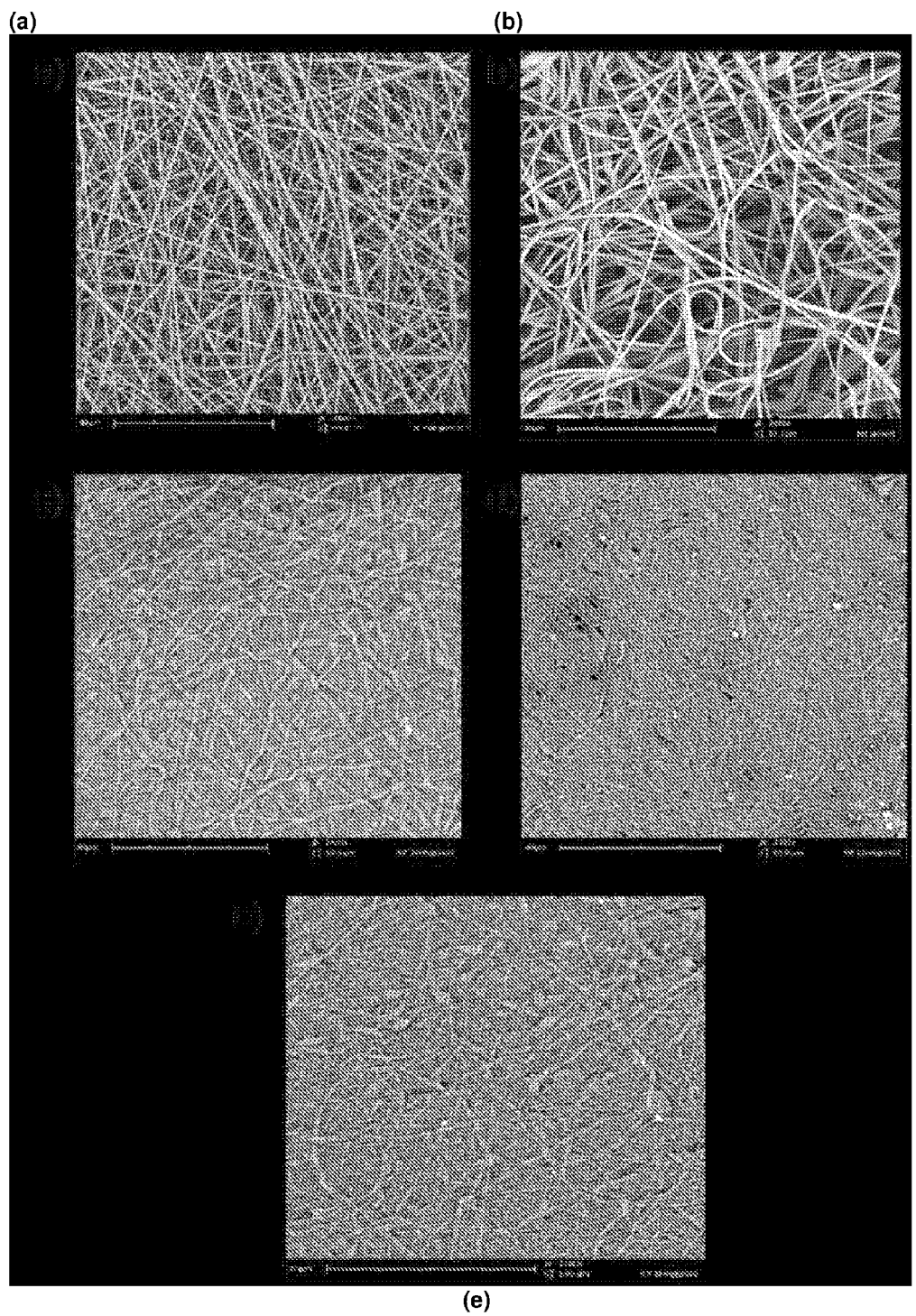
FIG. 16: shows scanning electron micrographs of a) formulation 6, b) formulation 7, c) formulation 8, d) formulation 9 and e) formulation 10.

Comparison between FIG. 16a and FIG. 16b demonstrated a drastic increase in the fiber diameter of 297.5±29.47 nm to 631±57.78 nm in non-RIF loaded and RIF-loaded nanofibers respectively. The increase in diameter correlates to the large increase in the viscosity of the RIF-loaded PVA solution. RIF-loaded nanofibers were deposited on the aluminium collector in a haphazard fashion with many bends and kinks in the fiber structure, as opposed to straighter and more uniform fibers deposited in non-drug loaded nanofibers. Comparison between FIG. 15a and FIG. 15b demonstrated that the addition of INH showed negligible differences in the fiber morphology and fiber diameter. Only a slight increase in the diameter from 345.00±30.41 nm to 372.5±28.61 nm was demonstrated.

Variations in the packing of the nanofibers were demonstrated in crosslinked and non-crosslinked nanofibrous membranes. Crosslinking "contracted" nanofibers producing a denser membrane with closely packed nanofibers, illustrated in FIGS. 15c-15e, and FIGS. 16c-16e. This further facilitated prolonged drug release characteristics of the crosslinked nanofibers. At the points of contact between individual nanofibers, crosslinking caused fibers to "fuse" together, substantiating that crosslinking does not occur only within single nanofibers, but between individual nanofibers as well.

PVA:GA Structural Interactions as a Result of Nanofiber Crosslinking

The possibilities of chemical and physical interactions as a result of crosslinking were evaluated using FTIR. Furthermore, if one considers the process of electrospinning of aqueous polymer solutions, it is of interest to ascertain to what extent the nature of the native polymer is modified. Examination of the FTIR spectra generated for the non-crosslinked PVA nanofibers (FIG. 17b) demonstrated that the electrospinning procedure had a minimal impact on conferring inter- or intra-molecular arrangements, with no band shifts or enhancements observed as compared to pure PVA (FIG. 17a).

Figure 17:
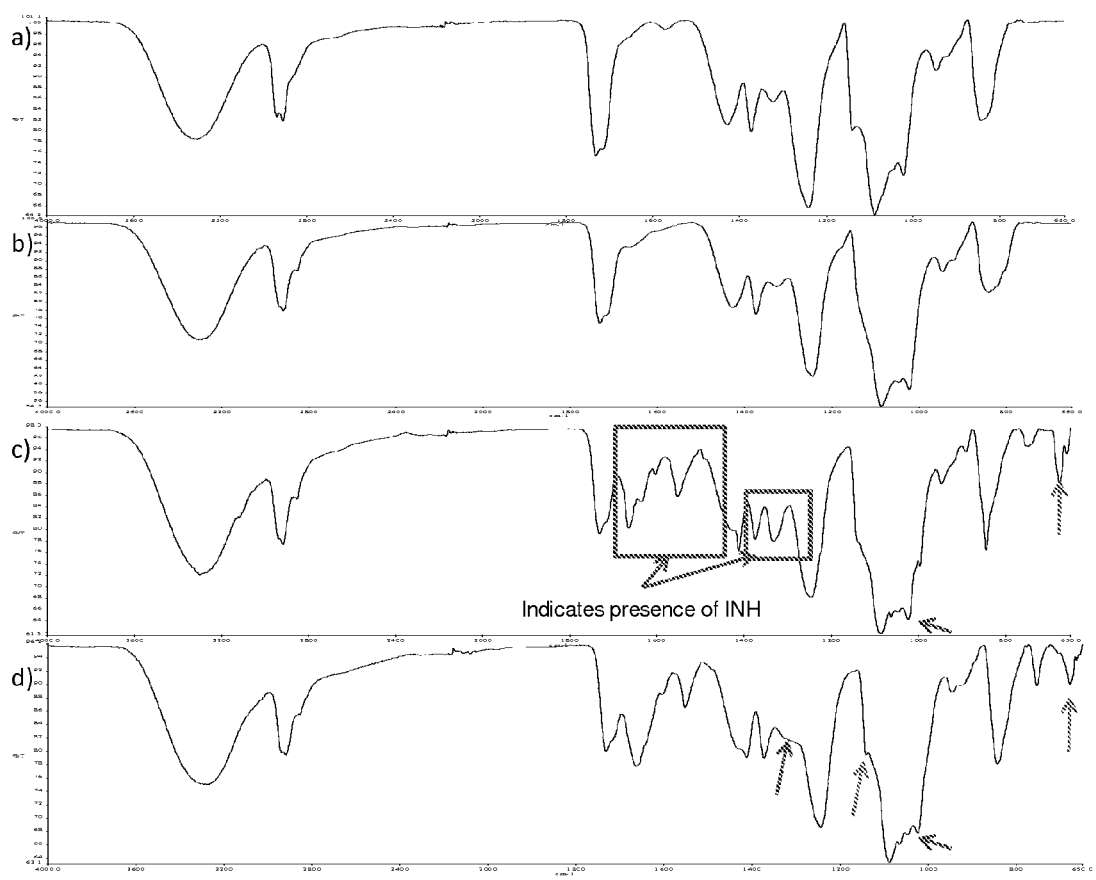
FIG. 17: shows FTIR spectra of a) Pure PVA, b) Formulation 1, c) Formulation 2 and d) Formulation 5. The red arrow indicates transmittance bands at 1380 $cm^{-1}$ and 1030 $cm^{-1}$ associating with C—OH stretching of PVA; the green arrow indicates transmittance band at 700 $cm^{-1}$ associating with O—H bonding in PVA, the blue arrow indicates transmittance band 1150 $cm^{-1}$ associating with C—O—C groups formed through crosslinking.

Crosslinking, on the other hand, had an impact on the establishment of inter- or intra-molecular crosslinks and is demonstrated by the variations in band intensities. As illustrated in FIG. 17, crosslinking of PVA with GA occurs through the formation of a —C—O—C— between the —OH of a typical PVA structure and the —C— of a GA molecule. As illustrated in FIGS. 17c and 17d, the transmittance bands at 1380 $cm^{-1}$ and 1030 $cm^{-1}$ (highlighted with a red arrow), indicative of C—OH bonding and the transmittance band at 700 $cm^{-1}$ (highlighted by a green arrow), indicative of an O—H bond decreases in intensity after crosslinking. The appearance of a peak/shoulder at 1150 $cm^{-1}$ (highlighted by a blue arrow) is indicative of —C—O—C— bonds which are formed during the crosslinking reaction. Furthermore, the strengthening of the transmittance band at 800 $cm^{-1}$ and 1720 $cm^{-1}$ is indicative of CH out of plane bending and C=O bonds respectively, is characteristic of GA. These results indicate the decrement of C—OH bonds in the PVA molecular structure allowing for the increment of C—H alkyl groups, thereby confirming that crosslinking between PVA and GA occurs. The additional peaks seen in the FTIR spectra of INH-loaded PVA nanofibers (FIG. 17c); not present in FIG. 17d spectra of non-drug loaded PVA nanofibers; is indicative of the presence of INH.

Figure 18:
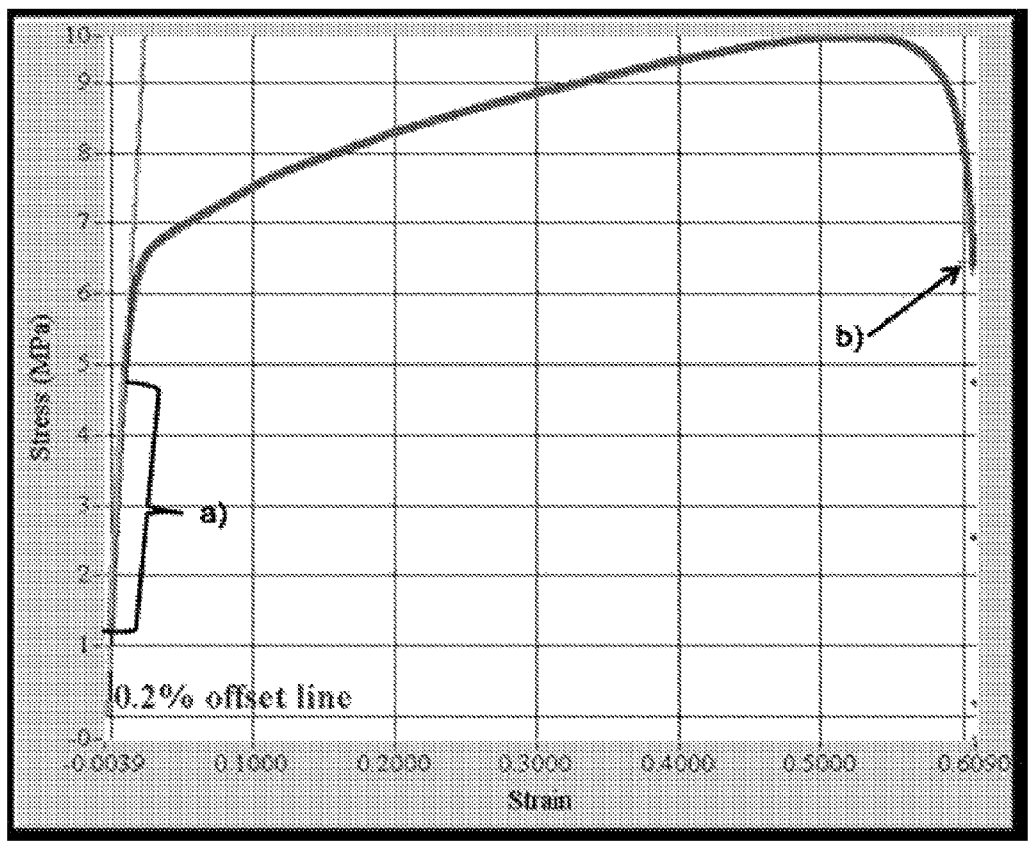
FIG. 18: shows a typical stress-strain nanotensile profile where a) is the linear portion of the slope from which Young's Modulus is determined; and b) depicts the fracture point of the sample.

Tensile Properties and Young's Modulus of Crosslinked and Non-Crosslinked Nanofibrous Membranes The stress-strain relationship of a material is highly dependent on the flexibility of the polymer chains and the strength of the material. When only a small amount of stress is required to produce a large amount of strain, the material is considered to be flexible and the Young's modulus, which is the slope of the linear portion of the stress-strain curve, as illustrated in FIG. 18, will be relatively small. A material is considered to be quite stronger than another when the ultimate strength, which is the maximum point on the stress-strain curve, is relatively higher. The average experimental values for Young's modulus (E), yield stress ($\sigma_y$) (magnitude of stress on the stress-strain curve at which appreciable deformation takes place without any appreciable increase in the stress), ultimate strength ($\sigma_u$) (the maximum stress a material can withstand), ultimate strain ($\epsilon_u$) and toughness ($u_t$) are outlined in Table 7.

TABLE 7

Experimental values obtained from nanotensile analysis of the crosslinked and non-crosslinked fibres

| Formulation | E (MPa) | $\sigma_y$ (MPa) | $\sigma_u$ (MPa) | $\epsilon_u$ | $u_f$ (J/cm$^{-3}$) |
|---|---|---|---|---|---|
| 1 | 401.295 | 8.555 | 10.78 | 0.399 | 3.89 |
| 2 | 91.330 | 3.960 | 4.860 | 0.4455 | 1.465 |
| 3 | 254.755 | 8.375 | 9.845 | 0.2595 | 0.81 |
| 4 | 253.155 | 6.220 | 8.710 | 0.4370 | 2.970 |
| 5 | 283.440 | 6.465 | 9.245 | 0.5605 | 4.320 |
| 6 | 111.545 | 2.31 | 3.745 | 0.609 | 1.63 |
| 7 | 37.695 | 1.495 | 3.755 | 1.3130 | 3.990 |
| 8 | 267.865 | 3.965 | 4.535 | 0.0400 | 3.965 |
| 9 | 284.98 | 2.575 | 7.90 | 0.206 | 0.88 |
| 10 | 189.760 | 4.750 | 6.335 | 0.6280 | 3.545 |

Figure 19:
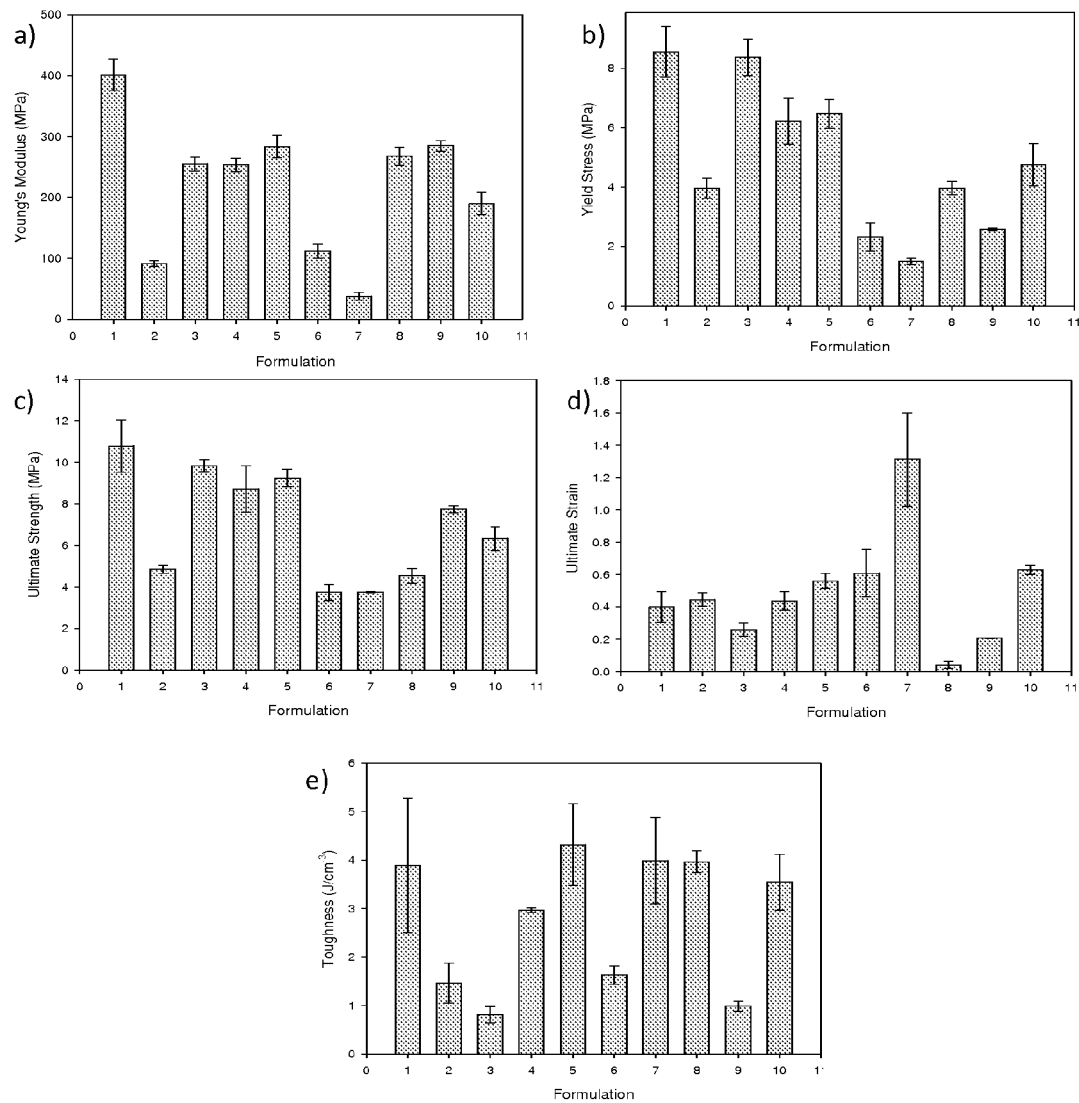
FIG. 19: is a vertical bar chart each outlining variations between the 10 formulations of a) Young's Modulus (E; MPa); b) Yield Stress ($\sigma_y$: MPa); c) Ultimate Strength ($\sigma_u$: MPa); d) Ultimate Strain ($\epsilon_u$); e) Toughness ($u_t$: J/cm-3) of Formulations 1-10.

As illustrated in FIG. 19, addition of drug caused a drastic decrease in the Young's Modulus of the PVA nanofibers, which is related to an increase in the elasticity of the nanofibrous membranes. The elasticity increase may be due to the plasticizing effect the drugs have on the nanofibers.

Non-crosslinked drug-loaded nanofibers demonstrated high variation in the elastic properties when differing concentrations of PVA were electrospun. A Young's Modulus of 91.330±4.67 MPas and 37.695±6.02 MPas were obtained for fibers electrospun from PVA solutions of concentrations 10% w/v and 8% w/v respectively. This variation in elasticity can be attributed to the differing fiber diameters illustrated in FIGS. 15b and 16b. Non-crosslinked drug loaded nanofibers demonstrated higher elasticity properties than crosslinked drug loaded nanofibers. This can be attributed to the nanofibers slipping pass one another, and aligning along the tensile pull axis. Crosslinking showed a distinct decrease in the elasticity of the nanofibers, which can be attributed nanofibers being unable to slip pass each other due to crosslinks caused between individual fibers, thus increasing the stiffness of the nanofibers.

Addition INH caused a substantial decrease in the ultimate strength of the nanofibers from 10.78±1.26 MPas to 4.86±0.20 MPas, whereas addition of RIF showed an insignificant change in the ultimate strength of the material. Crosslinking improved the strength of the drug-loaded nanofibers from 3.755±0.015 MPas to ultimate strengths ranging from 4.535±0.345 MPas to 7.92±0.02 MPas for RIF-loaded nanofibers and 4.86±0.2 MPas to ultimate strengths ranging from 8.71±1.12 MPas to 9.245±0.415 MPas for INH-loaded nanofibers.

Although, crosslinking improved the ultimate strength and stiffness of drug-loaded samples, crosslinking of RIF-loaded nanofibrous membranes produced very brittle membranes as they fail in tension at relatively low values of strain.

CONCLUSIONS

This study investigated the potential of a membrane system to improve the oral bioavailability of poorly absorbed drugs or enzyme-sensitive bioactive agents. Membranous drug delivery systems were shown to have the potential to increase the gastric residence time of drugs by incorporating mucoadhesive properties into the system. This application also describes a novel approach for an electrospinning technique. Electrospinning proved to be a versatile technique in fabricating drug-loaded PVA nanofibers, ideal for prolonged drug delivery. Modification through crosslinking using GA vapors produced relatively less-toxic PVA nanofibers possessing properties which are ideal for prolonged drug delivery. The PVA nanofibers demonstrated good drug loading capabilities and drug release kinetics which are important factors in drug delivery, and showed an improvement in the overall strength of the nanofibrous membranes.

REFERENCES

1. Grabovac V, Föger F, Bernkop-Schnürch A. Design and in vivo evaluation of a patch delivery system for insulin based on thiolated polymers, *International Journal of Pharmaceutics* 348 (2008) 169-174.
2. Helliwell M. The use of bioadhesives in targeted delivery within the gastrointestinal tract, *Advanced Drug Delivery Reviews*, 11 (1993) 221-251.
3. Davis S S. Formulation studies for absorption windows, *Drug delivery technology*, 10, No 4, (2005).
4. Shen Z and Mitragotri S. Intestinal Patches for Oral Drug Delivery, *Pharmaceutical Research*, 19, No. 4, (2002).
5. Nakamura K, Nara E, Akiyama Y. Development of an oral sustained release drug delivery system utilizing pH-dependant swelling of carboxyvinyl polymer, *Journal of Controlled Release* 111 (2006) 309-315.
6. Stamatialis D F, Papenburg B J, Giron'es M, Saiful S, Bettahalli S N M, Schmitmeier S, Wessling M. Medical applications of membranes: Drug delivery, artificial organs and tissue engineering, *Journal of Membrane Science* 308 (2008) 1-34.
7. Patel J K, Patel M M. Stomach Specific Anti-*Helicobacter Pylori* Therapy: Preparation and Evaluation of Amoxicillin-Loaded Chitosan Mucoadhesive Microspheres, *Current Drug Delivery*, 4 (2007), 41-50.
8. Guggi, D. et al. Systemic peptide delivery via the stomach: in vivo evaluation of an oral dosage form for salmon calcitonin. *Journal of Controlled Release* 92, (2002) 125-135.
9. Schmitz T, Leitner V M, Bernkop-SchnÜ A. Oral Heparin Delivery: Design and In Vivo Evaluation of a Stomach-Targeted Mucoadhesive Delivery System, Published online in Wiley InterScience. (www.interscience.wiley.com). DOI 10.1002/jps.20311
10. Eiamtrakarn S, Itoh Y, Kishimoto J, Yoshikawa Y, Shibata N, Murakami M, Takada K. Gastrointestinal mucoadhesive patch system (GI-MAPS) for oral administration of G-CSF, a model protein, *Biomaterials*, 23 (2002) 145-152.
11. Sill T J, von Recum H A. Electrospinning: Applications in drug delivery and tissue engineering, *Biomaterials* 29 (2008) 1989-2006.
12. Frenot A and Chronakis I S. Polymer nanofibers assembled by electrospinning, *Current Opinion in Colloid and Interface Science* 8 (2003) 64-75.
13. Kim T G, Lee D S, Park T G. Controlled protein release from electrospun biodegradable fiber mesh composed of poly(caprolactone) and poly(ethylene oxide), *International Journal of Pharmaceutics* 338 (2007) 276-283.

14. Schmaljohann D. Thermo- and pH responsive polymers in drug delivery, *Advanced Drug Delivery Reviews* 58 (2006) 1655-1670.
15. Hennink W E, van Nostrum C F, Novel crosslinking methods to design Hydrogels, *Advanced Drug Delivery Reviews* 54 (2002) 13-36.
16. Rastogi R, Sultana Y, Aqil M, Ali A, Kumar S, Chuttani K, Mishra A K. Alginate microspheres of isoniazid for oral sustained drug delivery, *International Journal of Pharmaceutics* 334 (2007) 71-77.

The invention claimed is:

1. An oral pharmaceutical dosage form for the release of at least two pharmaceutically active agents to different regions of the gastro intestinal tract, the pharmaceutical dosage form consisting of:
   (1) a first gastric pharmaceutical dosage component said gastric component consisting of:
      (a) a mucoadhesive layer which is capable of adhering to the gastro intestinal tract or buccal mucosa of the human or animal body, wherein the mucoadhesive layer of the gastric component is configured to adhere to the wall of the stomach when in use;
      (b) a water-insoluble outer layer; and
      (c) an intermediate layer positioned between the mucoadhesive and water-insoluble outer layers, wherein the water-insoluble outer layer of the gastric component ensures unidirectional release of pharmaceutically active agent from the intermediate and/or the mucoahesive layer to the gastric region;
      wherein the pharmaceutically active agent is incorporated into the intermediate and/or the mucoadhesive layer in the form of micro- and/or nano-fibers that are produced by electrospinning and crosslinking;
   (2) a second intestinal pharmaceutical dosage component, said intestinal component consisting of:
      (a) a mucoadhesive layer which is capable of adhering to the gastro intestinal tract or buccal mucosa of the human or animal body, wherein the mucoadhesive layer of the intestinal component is configured to adhere to the intestinal wall;
      (b) a water-insoluble outer layer; and
      (c) an intermediate layer positioned between the mucoadhesive and water-insoluble outer layers, wherein the water-insoluble outer layer of the intestinal component ensures unidirectional release of pharmaceutically active agent from the intermediate and/or the mucoadhesive layer to the intestine;
      wherein the pharmaceutically active agent is incorporated into the intermediate and/or the mucoadhesive layer in the form of micro- and/or nano-fibers that are produced by electrospinning and crosslinking;
   (3) a pH responsive polymeric layer connecting the first gastric pharmaceutical dosage component and the second intestinal pharmaceutical dosage component, said pH responsive layer located between the mucoadhesive layer of the intestinal component and the water-insoluble outer layer of the gastric component, said pH responsive polymeric layer causing the first gastric pharmaceutical dosage component and the second intestinal pharmaceutical dosage component to separate after ingestion from each other.

2. The pharmaceutical dosage form according to claim 1, wherein each dosage component comprises two or more intermediate layers, each intermediate layer comprising an active agent.

3. The pharmaceutical dosage form according to claim 1, wherein, in each one of the dosage components, one or more of the mucoadhesive layer, intermediate layer and water-insoluble outer layer is in the form of a polymeric membrane.

4. The pharmaceutical dosage form according to claim 1, wherein, in each one of the dosage components, one or more of the mucoadhesive layer, intermediate layer and water-insoluble outer layer is formed from a stimulus-responsive polymer which targets the pharmaceutical dosage component to a specific region of the gastro intestinal tract.

5. The pharmaceutical dosage form according to claim 4, wherein the different regions of the gastro intestinal tract are the gastric region and the intestinal region.

6. The pharmaceutical dosage form according to claim 1, wherein, in each one of the dosage components, each layer is independently formed from one or more polymer selected from the group consisting of polyethylene oxide (PEO), polyvinyl alcohol (PVA), ethylcellulose (EC), poly(lactic) co-glycolic acids (PLGA), polylactic acids (PLA), polymethacrylates, polycaprolactones, polyesters and polyamides.

7. The pharmaceutical dosage form according to claim 3, wherein, in each one of the dosage components, the polymers forming at least one of the polymeric membranes are crosslinked so as to retard the release of the active agent from the pharmaceutical dosage component.

8. The pharmaceutical dosage form according to claim 3, wherein, in each one of the dosage components, the polymers forming at least one of the polymeric membranes are selected so as to render the pharmaceutical dosage component pH responsive and to thus facilitate delivery of the active agent to a specific region.

9. The pharmaceutical dosage form according to claim 1, wherein, in each one of the dosage components, the mucoadhesive layer comprises a polymeric membrane formed from at least one mucoadhesive polymer selected from the group consisting of polyacrylic acid, chitosan, pectin, hydroxypropylcellulose (HPC), hydroxypropylmethylcellulose (HPMC) and hydroxyethylcellulose (HEC).

10. The pharmaceutical dosage form according to claim 1, wherein, in each one of the dosage components, the mucoadhesive layer additionally comprises a permeation enhancer.

11. The pharmaceutical dosage form according to claim 1, wherein, in each one of the dosage components, the mucoadhesive layer comprises at least one stimulus-responsive polymer which targets the pharmaceutical dosage component to a specific region of the gastro intestinal tract.

12. The pharmaceutical dosage form according to claim 11, wherein the different regions of the gastro intestinal tract are the gastric region and the intestinal region.

13. The pharmaceutical dosage form according to claim 1, wherein, in each one of the dosage components, the water-insoluble outer layer comprises a hydrophobic polymer which inhibits the release of the active agent.

14. The pharmaceutical dosage form according to claim 1, wherein, in each one of the dosage components, the water-insoluble outer layer comprises a hydrophobic polymer which protects the pharmaceutical dosage component from enzymatic or acid degradation in the gastro intestinal tract.

15. The pharmaceutical dosage form according to claim 1, wherein, in each one of the dosage components, the water-insoluble outer layer comprises at least one polymer selected from the group consisting of polyyamides, ethylcellulose (EC), cellulose acetate phthalate (CAP), polyacrylonitriles, polypropylene oxides and polycaprolactones.

16. The pharmaceutical dosage form according to claim 1, wherein, in each one of the dosage components, the water-insoluble outer layer additionally comprises at least one enzyme inhibitor to inhibit enzymatic degradation of the pharmaceutical dosage component.

17. The pharmaceutical dosage form according to claim 1, wherein the active agent is selected from one or more of the group consisting of anti-inflammatories, corticosteroids, antidiarrhoeals, opioids, immunosuppressives, antibiotics, antiemetics, antifungals, antivirals, antimalarials, anti-TB drugs, antiretrovirals, antihypertensives, proteins, peptides, chemotherapeutics, diagnostic agents, probiotics, prebiotics, multivitamins, minerals, trace elements, phytonutrients, proteins and peptides.

18. The pharmaceutical dosage form according to claim 1, wherein the active agent is a narrow absorption window drug.

19. The pharmaceutical dosage form according to claim 18, wherein the narrow absorption window drug is selected from the group consisting of acyclovir, bisphosphonates, captopril, furosemide, metformin, gabapentin, levodopa, baclofen and ciprofloxacin, or a combination thereof.

20. The pharmaceutical dosage form according to claim 1, which is formulated for oral drug delivery.

21. The pharmaceutical dosage form according to claim 1, which is formulated for oral delivery, configured to target the delivery of at least one active agent of at least one pharmaceutical dosage component to the buccal mucosa.

22. The pharmaceutical dosage form according to claim 6, wherein the one dosage component is for delivering an active agent to the gastric region of the gastro intestinal tract and the second dosage component is for delivering an active agent to the intestinal region of the gastro intestinal tract.

23. A method of forming the pharmaceutical dosage form as claimed in claim 1, the method comprising the steps of:

forming a mucoadhesive polymer layer which is capable of adhering to the gastro intestinal tract or buccal mucosa of a human or animal body;

forming an intermediate polymer layer comprising a pharmaceutically active agent, wherein the intermediate layer is formed by electrospinning micro- and/or nano-fibers containing the pharmaceutically active agent onto the mucoadhesive layer, and wherein the micro- or nano-fibers are cross-linked during the electrospinning; and covering the intermediate polymer layer with a water-insoluble outer layer.

24. The method of forming the pharmaceutical dosage form according to claim 23, wherein the mucoadhesive polymer layer is formed by electrospinning micro- and/or nano-fibers containing the pharmaceutically active agent, and wherein the micro- or nano-fibers are cross-linked during the electrospinning.

25. A method of administering a pharmaceutically active agent to a human or animal, the method comprising the step of administering a dosage forms as claimed in claim 1 to the human or animal, wherein the mucoadhesive layer of the dosage form adheres to the wall of the stomach or another region of the gastrointestinal tract, thus preventing premature gastric emptying, duodenal emptying, intestinal emptying, or colonic emptying of the dosage form; and the pharmaceutically active agents are released in a pH-responsive and time dependent manner to the gastrointestinal tract.

* * * * *